(12) United States Patent
Hayashida

(10) Patent No.: US 7,394,925 B2
(45) Date of Patent: Jul. 1, 2008

(54) RADIOGRAPHY APPARATUS AND RADIOGRAPHY METHOD

(75) Inventor: Shinsuke Hayashida, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 883 days.

(21) Appl. No.: 10/863,566

(22) Filed: Jun. 8, 2004

(65) Prior Publication Data

US 2004/0258201 A1    Dec. 23, 2004

(30) Foreign Application Priority Data

Jun. 18, 2003  (JP)  .............................. 2003-172868

(51) Int. Cl.
*G06K 9/00* (2006.01)
*G01N 23/04* (2006.01)

(52) U.S. Cl. ........................... 382/132; 382/128; 378/62

(58) Field of Classification Search ................. 382/132, 382/128; 378/62
See application file for complete search history.

(56) References Cited

U.S. PATENT DOCUMENTS 5,974,113 A * 10/1999 Bruijns et al. .............. 378/98.7

6,497,511 B1 * 12/2002 Schmitt et al. .............. 378/207
6,516,098 B2   2/2003 Nonaka
6,643,411 B2  11/2003 Nonaka
2002/0087074 A1  7/2002 Nicolas

FOREIGN PATENT DOCUMENTS

| JP | 04-181882 | 6/1992 |
| JP | 07-281329 | 10/1995 |
| JP | 11-151233 A | 6/1999 |
| JP | 11-218858 | 8/1999 |

* cited by examiner

*Primary Examiner*—Bhavesh Mehta
*Assistant Examiner*—Jonathan C Schaffer
(74) *Attorney, Agent, or Firm*—Canon U.S.A., Inc., IP Division

(57) ABSTRACT

A radiography apparatus with a function for evaluating image quality is provided. To accomplish this, the radiography apparatus includes a radiating-generating unit for emitting radiation, an imaging unit for converting the radiation into image data, a measuring unit for measuring an image-quality evaluating value of the image data, and a determining unit for determining the image quality of the imaging unit based on a plurality of image-quality evaluating values of the image data acquired at a plurality of points in time, where each image-quality evaluating value corresponds to the image data acquired at one of the points in time.

15 Claims, 20 Drawing Sheets

*1 : INDUCTIVE ESTIMATION FROM
    MEASUREMENT DATA IS NOT POSSIBLE.

RADIOGRAPHY APPARATUS AND RADIOGRAPHY METHOD

BACKGROUND OF THE INVENTION

1. Field of the Invention

The present invention relates to a radiography apparatus and a radiography method for acquiring image data with an imaging unit, and particularly to a radiography apparatus and a radiography method with a function for evaluating a degradation over time in quality of an image acquired with an imaging unit.

2. Description of the Related Art

In a known radiography apparatus, a radiation source emits a radiation beam onto an object to be analyzed, such as a medical patient. The radiation beam that has passed through the patient then enters a screen film cassette, a film autochanger, a computed radiography (CR) system, a flat panel detector (FPD), or the like for imaging. Radiographs are also rapidly becoming digital, just like other consumer products.

Recently, a technology has been developed for acquiring digital images by using an image-receiving unit called an FPD, which is a photoelectric converting unit having pixels such as small imaging elements or switching devices arranged in an array. Some advantages associated with the utilization of such a photoelectric converting unit are as follows. First, since images acquired are digital data, image processing, such as correction for undesirable radiographic conditions and enhancement of a region of interest, is easy. Furthermore, patients in a remote hospital without a specialist can be diagnosed by a specialist in a separate large hospital with an image-communicating unit via a large-capacity communication line. In addition, the storage space required for digital images is much smaller than the storage space required for images on film because digital image data can be stored on, for example, a magneto-optical disk. Yet another advantage is that it is easier to search for historical images stored in digital format, so that reference images can be presented more easily than when images on film are searched for, as described in Japanese Patent No. 3413084.

A typical radiography apparatus is subject to degradation in image quality as it repeats radiography over time, that is, as its operation time accumulates. Unfortunately, an objective invariance test for evaluating degradation in image quality over time has not yet been conducted in known radiography apparatuses.

SUMMARY OF THE INVENTION

There have been demands for various measures to address the problem of the quality of image data acquired by an imaging unit of a known radiography apparatus typically deteriorating over time.

In response to these demands, an object of the present invention is to provide a radiography apparatus with a function for evaluating a change over time in quality of an image acquired with an imaging unit.

According to an aspect of the present invention, a radiography apparatus includes a radiating-generating unit for emitting radiation, an imaging unit for converting the radiation into image data, a measuring unit for measuring an image-quality evaluating value of the image data, and a determining unit for determining the image quality of the imaging unit based on a plurality of image-quality evaluating values of the image data acquired at a plurality of points in time, where each image-quality evaluating value corresponds to the image data acquired at one of the points in time.

According to another aspect of the present invention, a radiography method includes a radiating-generating step of emitting radiation, an imaging step of converting the radiation into image data, a measuring step of measuring an image-quality evaluating value of the image data, and a determining step of determining the image quality of the imaging unit based on a plurality of image-quality evaluating values of the image data acquired at a plurality of points in time, where each image-quality evaluating value corresponds to the image data acquired at one of the points in time.

According to the present invention, a radiography apparatus with a function for evaluating a change over time in quality of images acquired by the imaging unit can be provided.

Other features and advantages of the present invention will be apparent from the following description taken in conjunction with the accompanying drawings, in which like reference characters designate the same or similar parts throughout the figures there.

DESCRIPTION OF THE PREFERRED EMBODIMENTS

A preferred embodiment of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
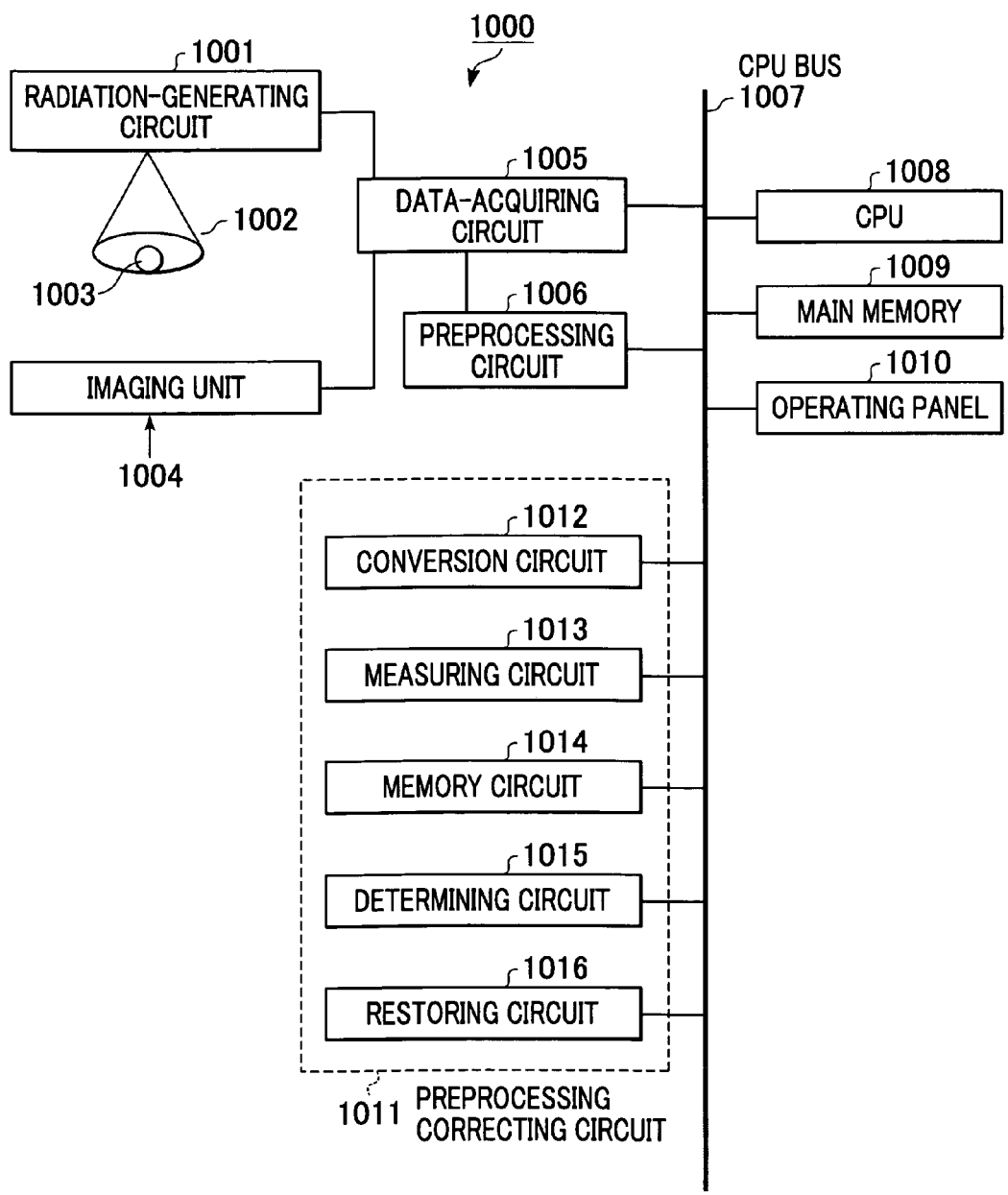
FIG. 1 shows the structure of a radiography apparatus according to a first embodiment.

FIG. 1 shows a radiography apparatus 1000 according to a first embodiment of the present invention. The radiography apparatus 1000 according to this embodiment has a function for objectively evaluating a change in image quality over time, particularly based on an image-quality evaluating value calculated from image data.

The radiography apparatus 1000 includes a radiation-generating circuit 1001 for emitting radiation; an imaging unit 1004 as imaging means for receiving the radiation and converting it to image data; a data-acquiring circuit 1005 for applying predetermined conversion to the image data; a preprocessing circuit 1006 for applying predetermined processing; and a preprocessing correcting circuit 1011 for calculating an image-quality evaluating value from image data and for performing restoration based on the image-quality evaluating value. The radiography apparatus 1000 further includes a CPU 1008, a main memory 1009, and an operating panel 1010. These circuits and units are controlled by the CPU 1008 and interconnected such that data is sent to/received from one another via a CPU bus 1007.

The preprocessing correcting circuit 1011 includes a measuring circuit 1013 for measuring an image-quality evaluating value based on image data; a memory circuit 1014 for storing image-quality evaluating values obtained at two or more different points in time; a determining circuit 1015 for determining the quality of an image acquired with the imaging unit 1004 based on the image-quality evaluating values obtained at the two or more different points in time, and a restoring circuit 1016 for restoring image data based on the determination result by the determining circuit 1015.

Figure 2:
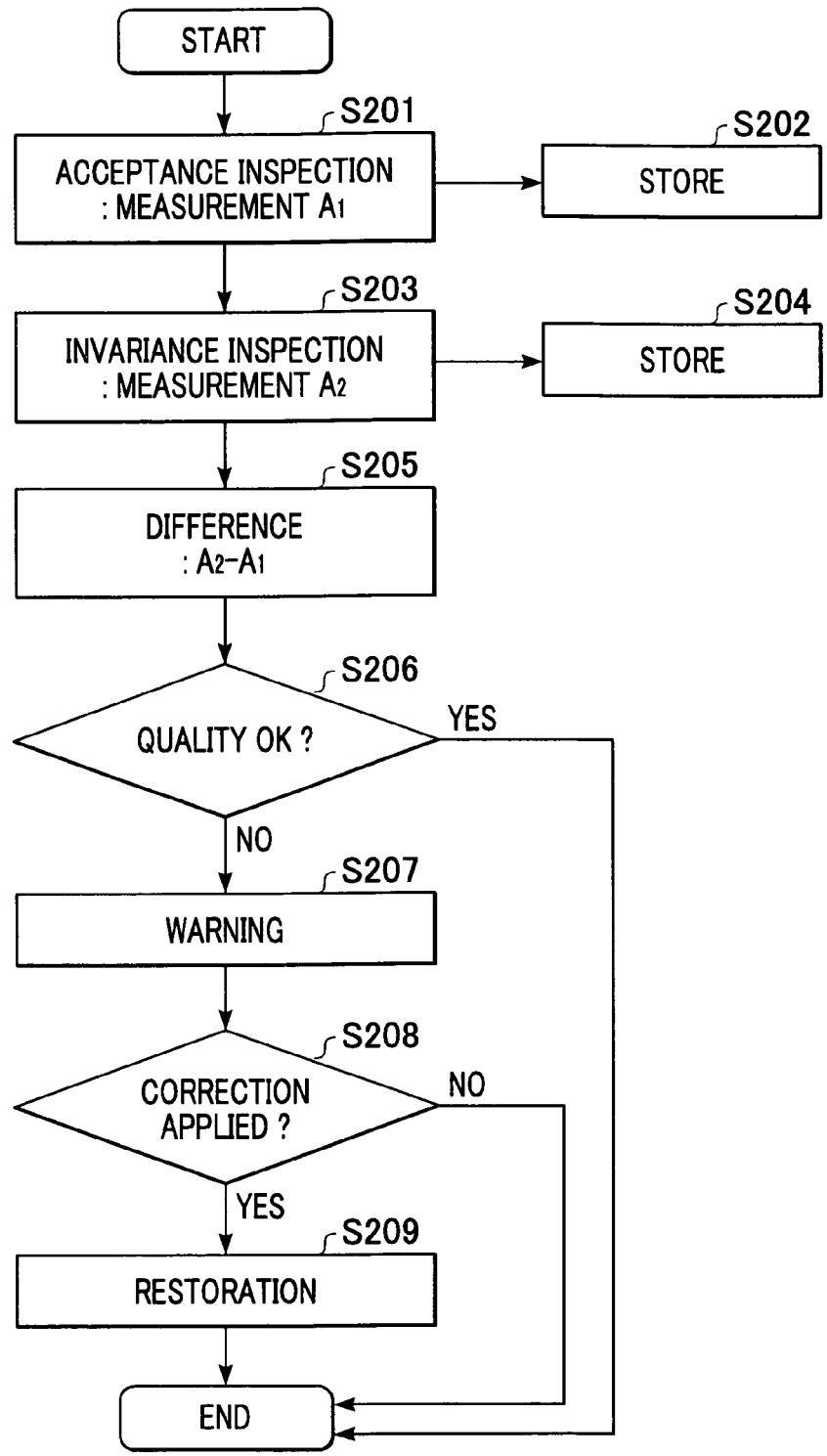
FIG. 2 is a flowchart where the number of defective elements is used as an image-quality evaluating value.

FIG. 2 is a flowchart diagram for evaluating a change in the number of defective elements over time and for performing restoration, according to this embodiment. FIGS. 3A to 3D are schematic diagrams showing the relationship between the degree of change in image quality and methods for evaluating image quality. Details of the relationship will be described later.

In the above-described radiography apparatus 1000, the main memory 1009 stores various types of data necessary for processing by the CPU 1008 and also functions as a work memory used by the CPU 1008. The CPU 1008 controls the entire operation of the radiography apparatus 1000 according to the instructions sent via the operating panel 1010, while using the main memory 1009. With the above-described CPU 1008, the radiography apparatus 1000 operates as follows.

Referring to FIG. 1, the radiation-generating circuit 1001 irradiates a subject (also referred to an object) 1003 with a radiation beam 1002. The radiation beam 1002 emitted by the radiation-generating circuit 1001 passes through the subject 1003, and the attenuated radiation beam 1002 enters a two-dimensional radiation sensor (not shown) within the imaging unit 1004. The imaging unit 1004 converts the radiation to image data and then outputs the image data to the data-acquiring circuit 105. The data-acquiring circuit 1005 converts the received image data output to a predetermined electrical signal, and passes the signal to the preprocessing circuit 1006. The preprocessing circuit 1006 applies preprocessing such as offset correction and gain correction to the image data received from the data-acquiring circuit 1005. Image data in this embodiment is not limited to that acquired by the imaging unit 1004. Instead, image data output from the data-acquiring circuit 1005 or the preprocessing circuit 1006 is also applicable. The data-acquiring circuit 1005 and the preprocessing circuit 1006 carry out, for example, adjustment of the dynamic range and other various types of correction. Thus, image quality evaluation may be applied to any output image data. Furthermore, the data-acquiring circuit 1005 and/or the preprocessing circuit 1006 may be included in the imaging unit 1004.

The operation of the preprocessing correcting circuit 1011 will now be described with reference to FIGS. 2, 4, and 6.

FIG. 2 is a flowchart showing the operation of the radiography apparatus 1000. For the operation according to the flowchart in FIG. 2, the main memory 1009 stores, for example, data and processing programs necessary for various types of processing by the CPU 1008 and also functions as a work memory used by the CPU 1008. In particular, the main memory 1009 stores the processing programs according to the flowchart show in FIG. 2. Thus, the CPU 1008 controls the following operation of the radiography apparatus 1000, by loading a program (e.g., a processing program according to the flowchart in FIG. 2) from the main memory 1009, and then executing the loaded program.

The flow starts in step S201 with an acceptance inspection, which is carried out after the installation of and before the use of the radiography apparatus 1000 in, for example, a hospital. In the acceptance inspection, the image quality exhibited by the imaging unit 1004 is evaluated when the radiography apparatus 1000 is operated for the first time. An image-quality evaluating value is a score of the quality of image data acquired by the imaging unit 1004. An image-quality evaluating value is obtained from image data acquired while a chart or a phantom suitable for the measurement of the image-quality evaluating value is placed, for example, between the radiation-generating circuit 1001 and the imaging unit 1004 or acquired with no shielding object placed in the radiation path.

In step S202, the image-quality evaluating value obtained in the acceptance inspection in step S201 is stored in the memory circuit 1014 along with data such as the images and measurement date/time. Here, measured physical quantities $A_n$, $B_n$, and $C_n$ indicate measurements at a point in time n, and A, B, and C indicate different types of measured physical quantity. An image-quality evaluating value may be a measured physical quantity itself or may be a calculated value produced as a result of some arithmetic operation on the measured physical quantity.

A certain period of time after the acceptance inspection has been completed, an image-quality evaluating value is measured again in step S203. Such an inspection carried out again at a later point in time is referred to as an invariance test. The interval at which the inspections are carried out is determined according to image-quality evaluation items. Such intervals may be in accordance with the specifications of, for example, the International Electrotechnical Commission (IEC) or Japanese Industrial Standards (JIS), if such standards specify inspection intervals. The inspection intervals may be appropriately determined by the user based on the user's experience(s). The inspection intervals can be set differently depending on the usage of the radiography apparatus 1000. For example, the inspection intervals may be set longer up to a halfway point of the warranty period from the purchase of the radiography apparatus 1000, and thereafter, the inspection intervals may set shorter. The inspection performed in step S203 is desirably identical to that of step S201.

In step S204, the image-quality evaluating value obtained at step S203 is stored in the memory circuit 1014. In addition, in order to store factors which can affect the measurements, information such as measurement date/time, temperature, and humidity are also stored.

Next, a comparison is made with the image-quality evaluating values stored at steps S202 and S204 to observe a change over time. Here, the number of types of image-quality evaluating value is not limited to one. Instead, there should be several types of image-quality evaluating values.

An example of an image-quality evaluating value will now be described with reference to a defect of an imaging element included in the imaging unit 1004. Some imaging elements have photoelectric characteristics different from those of normal imaging elements. These imaging elements are called defective elements. Among many types of defective elements, a typical defective element is characterized by a deterioration in photoelectric characteristics that is too serious to electrically respond to a certain degree of radiation.

One example of a method for comparing image-quality evaluating values is a calculation of differential value. The calculation of a differential value is effective to obtain, for example, a change in the area or the number of defective elements over time. The number of defective elements varies discretely, and imaging elements that are once determined to be defective rarely restore their normal function. For this reason, the calculation of a differential value is preferable in order to find such a numerical change in the number of defective elements (step S205). This differential value, as an image-quality evaluating value, indicates a change in the number of defective elements over time.

Next, in step S206, a determination is made in the determining circuit 1015 whether the differential value obtained in step S205 results from an actual change in an image-quality evaluating value or from a randomly varying factor. The determining circuit 1015 prestores, for example, a table of statistical data about differential values, and determines whether or not a change in the number of defective elements is significant according to the table.

If a determination is made that the change in an evaluation item is significant (i.e., there may be a problem with the image quality) in step S206, then in step S207, the user is informed via a display unit such as operating panel 1010 that some image-quality evaluating value (in this case, an increase in the number of defective elements or the area of the defective elements) has changed. The information provided to the user includes, but is not limited to, image-quality evaluating items, date/time, and the amount of change over time.

If a determination is made that the change in an evaluation value is significant in step S206, following the notification provided in step S207, the user in step S208 determines whether or not correction should be applied. Typically, there are two reasons why correction should be applied. First, the since radiography apparatus 1000 is typically used for medical diagnosis, it is therefore not desirable that the apparatus 1000 automatically change its settings. Second, the user should recognize that the image quality has changed as a result of correction. It is also acceptable, however, that the restoring circuit 1016 automatically starts restoration as soon as the image-quality evaluating value exceeds a predetermined value regardless of the operation by the user. In this case, the radiography apparatus 1000 is programmed so that restoration automatically starts as a result of the image-quality evaluating value exceeding a predetermined value.

The restoring circuit 1016 starts restoration in step S209 when the operator selects to carry out correction at step S208 or when the radiography apparatus 1000 is programmed so that restoration automatically starts as a result of the image-quality evaluating value exceeding a predetermined value. Correction is carried out, in particular, so that image-quality evaluating values at the time of the acceptance inspection are restored. A restoration procedure carried out when the number of defective elements (proportional to the area of the defective elements) increases is as follows: a defective element is located, the coordinates of the defective element are registered in a defect map, and defect correction is carried out by using the outputs from the normal imaging elements surrounding the defective element. Such defect correction is common, and a more detailed description is omitted. A further differential value (i.e., a second-order differential value) enables the trend of an increase in the number of defective elements over time to be evaluated. Thus, it is possible to objectively understand a variation in image quality over time by comparing image-quality evaluating values at different points in time.

Figure 3A:
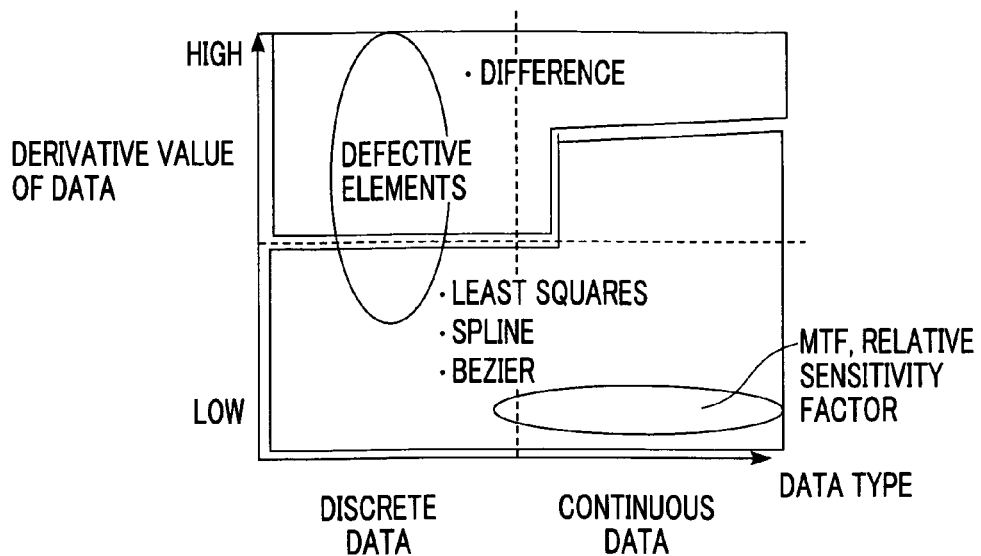
FIGS. 3A to 3D illustrate defective elements.
Figure 3B:
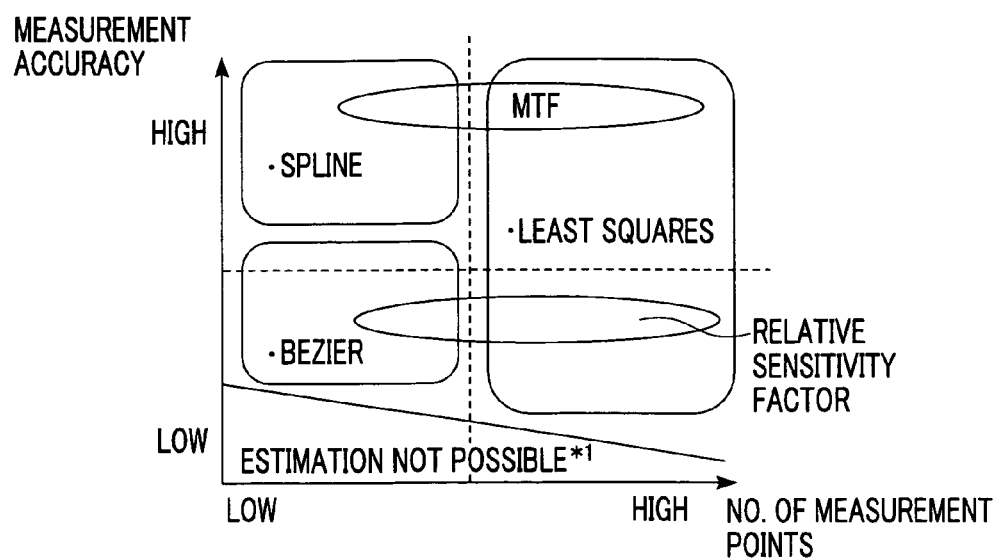

FIGS. 3A to 3D are schematic diagrams illustrating a change in the number of defective elements over time and several types of such defective elements. FIGS. 3A and 3B are examples of a matrix representing methods for estimating image-quality evaluating values over time.

In FIG. 3A, the horizontal axis represents types of image-quality evaluating values (discrete or continuous), and the vertical axis represents the amount of change over time as a degree of change in data. Here, discrete data indicates data that exhibits a discrete variation, such as the number of defective elements. On the other hand, continuous data indicates data that exhibits a continuous change in image-quality evaluating value. Continuous data includes a ratio of modulation transfer functions (MTFs), functioning as a sharpness-evaluating value, and a relative sensitivity factor (described below).

In the determining circuit 1015, a method for estimating a change in image-quality evaluating value over time is determined conceptually based on the matrices shown in FIG. 3A. A defective element resulting from a certain factor such as occurrence of linear defective elements may lead to a large derivative value over time. On the other hand, a sharpness-evaluating value such as a ratio of MTFs and a ratio of relative sensitivity factors change gradually over time. For an image-quality evaluating value that exhibits a large derivative value, which represents a change over time, a difference and a second-order difference are used to perform an estimation over time. This is because such a rapid discrete change cannot be estimated with other linear estimating methods.

For an estimation based on a differential value, a determination is made that the image quality deteriorates if a sharp change is seen in the differential value. In addition, an increase/decrease in image-quality evaluating value over time is also estimated by calculating a second-order differential value. In contrast, for example, a spline is used to obtain the relationship between image-quality evaluating values at different points in time and the elapsed time between such points in time, and hence can be used to estimate a future variation in image-quality evaluating value. For the sharpness-evaluating value (i.e., ratio of MTFs) and the ratio of relative sensitivity factors, which are continuous data and hence exhibit a small derivative value representing a change over time, a least squares method, a spline curve approximation, or a Bezier curve approximation is used. The variation in image-quality evaluating value at a future point in time is estimated based on these techniques. With this estimation, it is also possible to determine, for example, when to start restoration and the degree of restoration.

FIG. 3B is a schematic diagram showing how the determining circuit 1015 selects an appropriate estimating method based on the relationship between the number of measurement points and measurement accuracy.

The horizontal axis represents the number of measurement points of image-quality evaluating values, and the vertical axis represents the measurement accuracy of the image-quality evaluating values. The image-quality evaluating items are classified by the measurement accuracy along the vertical axis. The measurement accuracy is good with the sharpness-evaluating value such as the MTF, but is not so good with the relative sensitivity factor due to a change in the X-ray tube over time or a change in the dosimeter over time. For this reason, the sharpness-evaluating value, such as the MTF, is estimated by a spline curve approximation in the case of a small number of measurement points, and is estimated by a least squares method if the number of measurement points exceeds a certain value (indicated by "N" at step S411 in FIG. 4). The relative sensitivity factor is estimated by a Bezier curve approximation in the case of a small number of measurement points, and is estimated by a least squares method if the number of measurement points exceeds a certain value (indicated by "N" at step S609 in FIG. 6). The relative sensitivity factor does not exhibit very good measurement accuracy, that is, it exhibits a large change in accuracy depending on the measuring method. Thus, the relative sensitivity factor is estimated by a Bezier curve approximation in the case of a small number of measurement points, and is estimated by a least squares method if the number of measurement points is large. One of the reasons a Bezier curve is used as a method for estimating the relative sensitivity factor is that a spline curve, which passes through all measuring points, produces an estimated value that depends greatly on the values obtained at the end point and points near the end point. Criteria for methods of estimating image-quality evaluating values over time are not limited to those shown along the four axes in FIGS. 3A and 3B. Other criteria can also be used to select an estimation unit as estimation means according to the present invention. For example, the criteria can differ depending on different factors that cause a change in image-quality evaluating value or can be changed according to the measurement protocol of each facility.

Figure 3C:
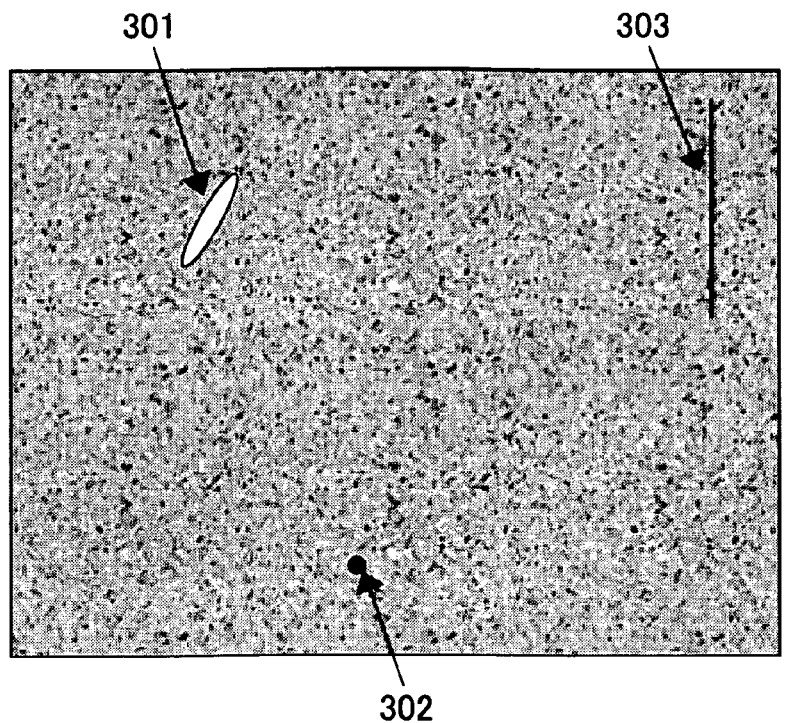

FIG. 3C is a diagram illustrating defective elements on an image. The types of defective elements include a flaw 301 on a fluorescent substance, a defective pixel 302, and a defective line 303. The flaw 301 on the fluorescent substance is caused by a mechanical interference, such as an external force being applied to the fluorescent substance. These images are characterized by surrounding pixels appearing inflated, a gradual decrease in pixel value compared with surrounding pixel values, etc. A short circuit of a bias line or a signal line in an imaging element causes the defective pixel 302, or the defective line 303. These flaws continue to appear in the form of defective elements until an appropriate hardware repair is completed.

Figure 3D:
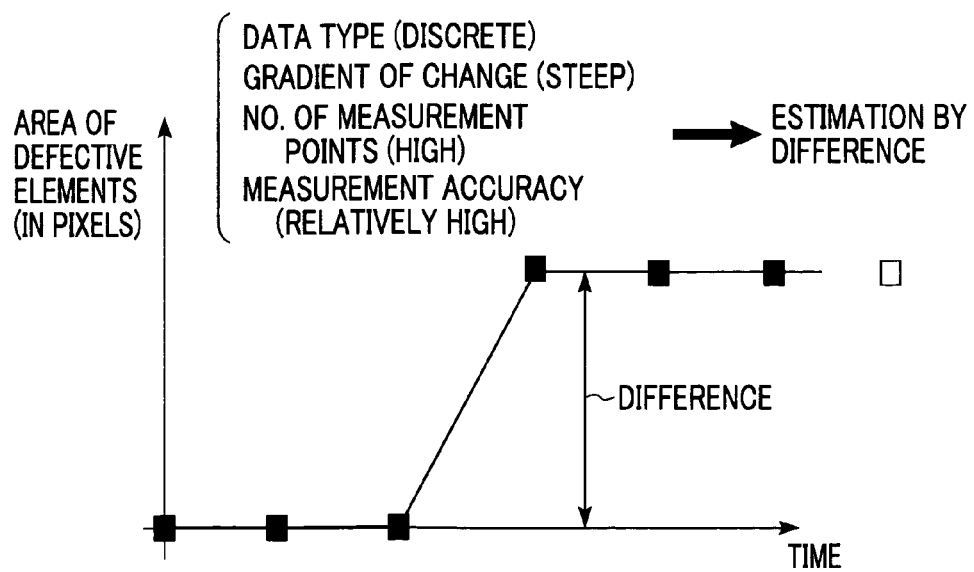

FIG. 3D shows a change in the area of defective elements represented as pixel value (proportional to the number of defective elements) over time. Causes of an increase in the number of defective elements include a flaw on a surface of the imaging unit 1004, a flaw on the CR imaging plate, a flaw on the fluorescent substance, a short-circuit of a bias line or a signal line of an imaging element. If one of these causes occurs, the number of defective elements may increase. In other words, if the area of the defective elements, which is used as an image-quality evaluating value, exceeds a certain value, the restoring circuit 1016 starts to apply restoration (i.e., correction of defective elements) to the image data.

At present, even if there is a flaw on a CR imaging plate, the radiographer uses the CR system as-is, taking the location of the flaw into mind without correcting the flaw through image processing. Thus, a CR system can be operated in the same manner as before by the user selecting in step S208 of FIG. 2 not to apply correction to the image-quality evaluating value associated with such a defective element.

Figure 4:
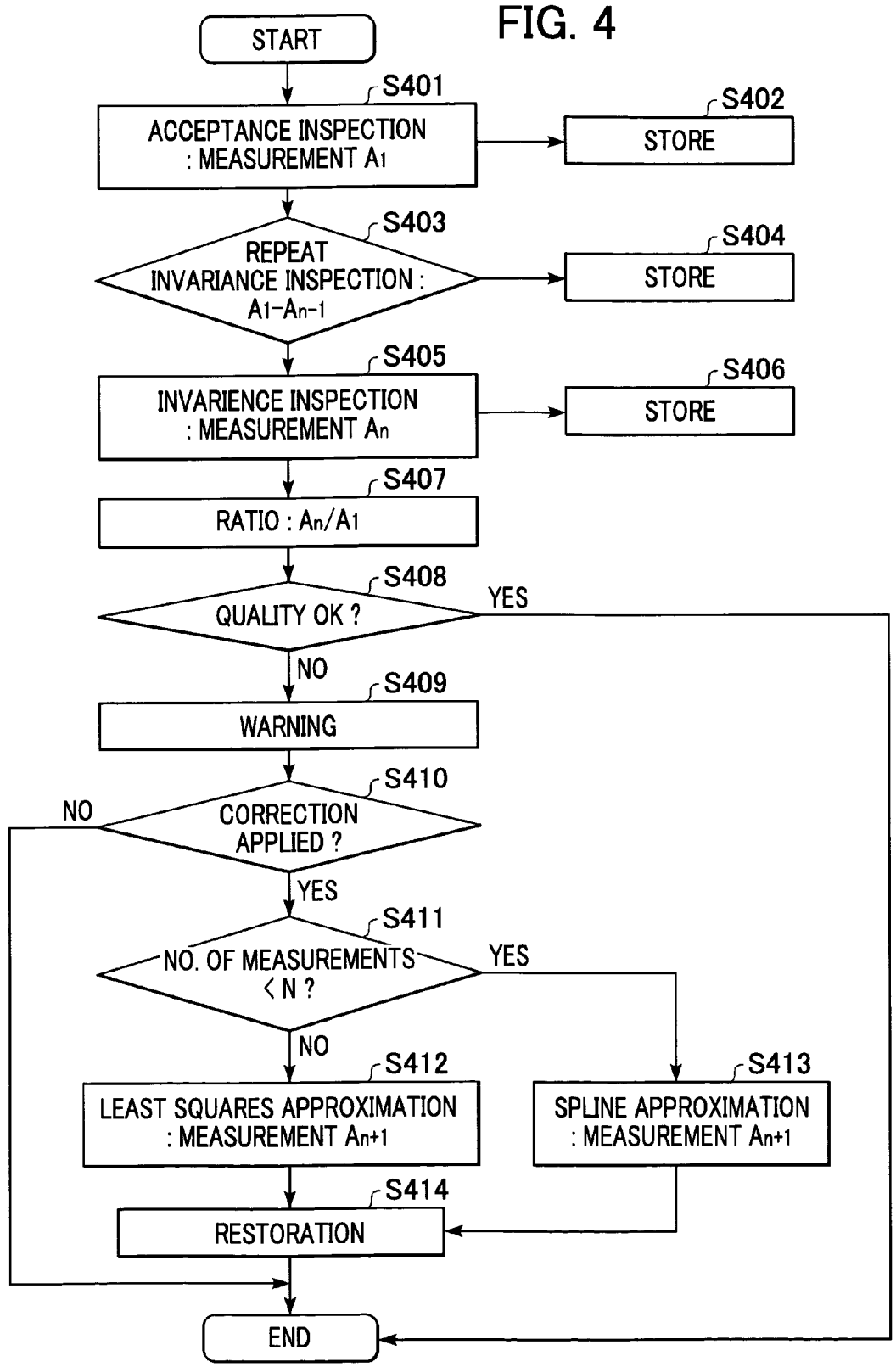
FIG. 4 is a flowchart where an MTF is used as an image-quality evaluating value.
Figure 5A:
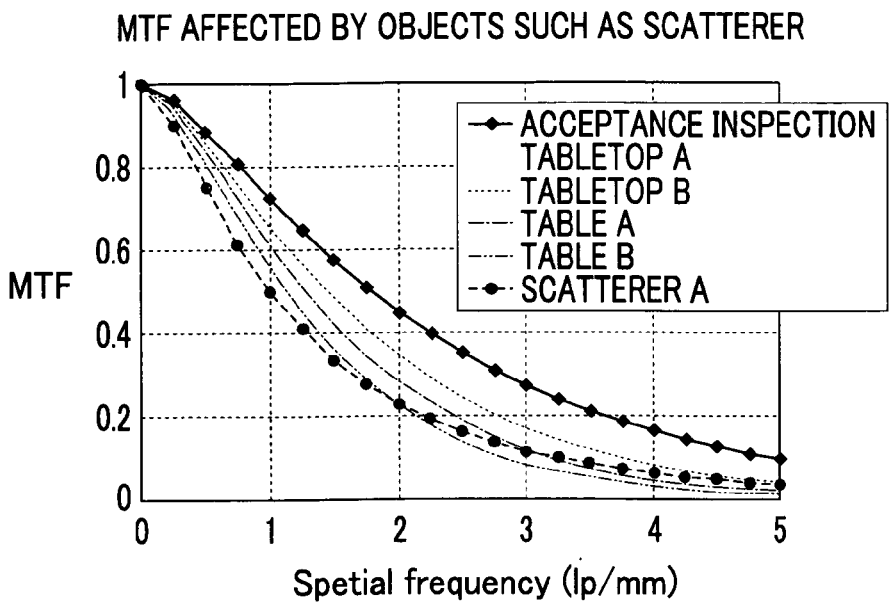
FIGS. 5A to 5F illustrate the MTF.

FIG. 4 shows the flow of processing for using the ratio of MTFs representing the sharpness-evaluating value as an image-quality evaluating value, and in particular a method for performing restoration by estimating a change over time by a least squares method. FIG. 5A illustrates the amount of degradation of the MTF. As an image-quality evaluating value, the MTF itself can be used. According to this embodiment, a ratio of MTFs can also be used as an image-quality evaluating value. A ratio is used for normalization.

FIG. 5A shows how tabletop B, table A, table B, and scatterer A affect the MTF after acceptance inspection. The horizontal axis represents spatial frequency, and the vertical axis represents the MTF value corresponding to the spatial frequency. The curve indicated by "ACCEPTANCE INSPECTION" represents the MTF measurement with the imaging unit 1004 only, whereas the curve indicated by "tabletop B" is the MTF when an image is acquired through the tabletop B. In this manner, the MTF is affected by the tabletop B, table A, table B, scatterer A, and the like, and therefore the MTF deteriorates as these components deteriorate.

In many cases, the information regarding a useful diagnostic image resides in the range from about 0.5 lp/mm to 2.0 lp/mm. Thus, a central value of the spatial frequency within this range may be used to find a change over time, or an image-quality evaluating value may be produced by weighting MTFs corresponding to various spatial frequencies. Also in this case, the MTF itself may be used or a ratio of MTFs may be used. In the following image-quality evaluating value, a ratio of measured physical quantities may be used for the normalization of units. In addition, a measured physical quantity itself can also be used.

Figure 5B:
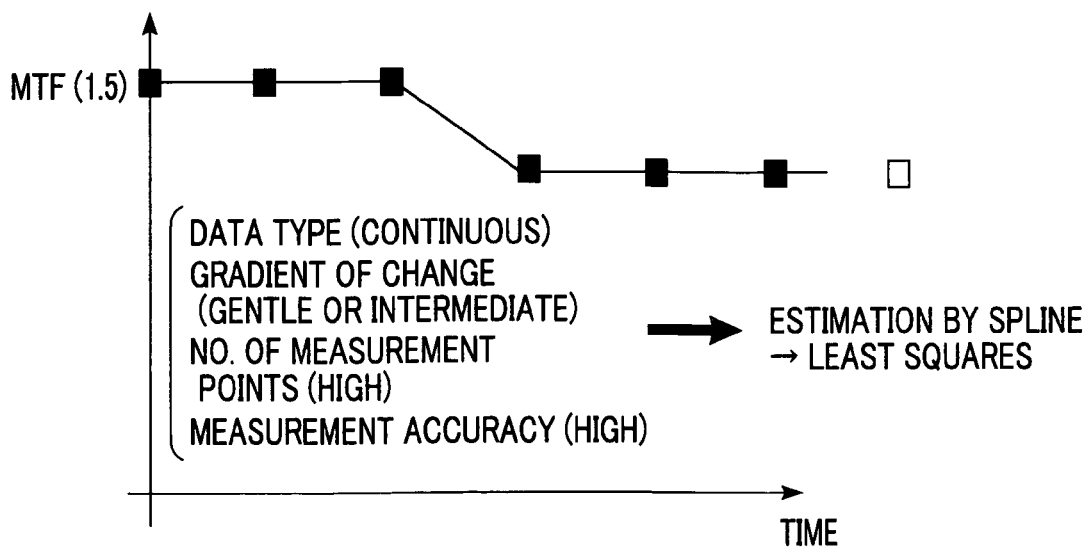

FIG. 5B is a schematic diagram showing a change in MTF over time at a particular frequency, for example, at 1.5 lp/mm. Measurements of MTF vary slightly with, for example, radiographic conditions other than changes over time. However, an accuracy of about ±0.1 standard deviation is achieved by using a method standardized by, for example, the IEC that ensures some degree of measurement accuracy. Therefore, if a change beyond a standard deviation of ±0.1 is measured, a determination can be made at step S408 of FIG. 4 that a change over time has occurred. In other words, at step S408 of the determining method according to the present invention, a determination is made as to whether an obtained measurement results from an actual change in an image-quality evaluating value or from a randomly varying factor. In this embodiment, a change over time is shown based on the MTF value at a spatial frequency of 1.5 lp/mm. The spatial frequency, however, is not limited to the above-described value. It is also acceptable to measure a change over time at another spatial frequency value. Furthermore, a comprehensive evaluating value may be produced within a certain range of frequencies by weighting MTFs corresponding to various spatial frequencies.

Figure 5C:
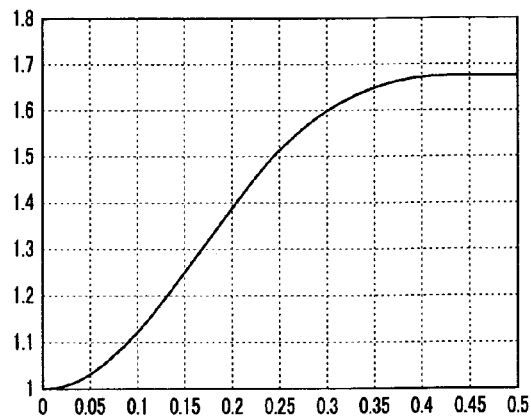
Figure 5D:
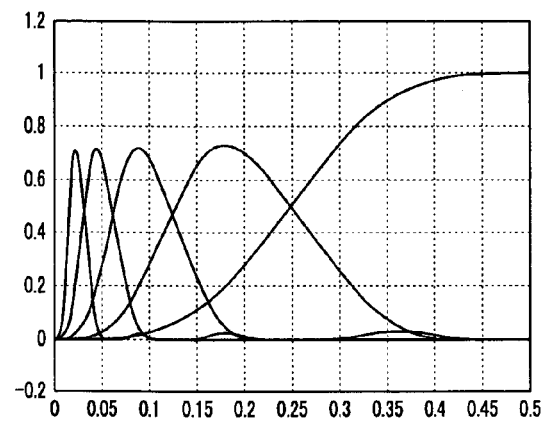
Figure 5E:
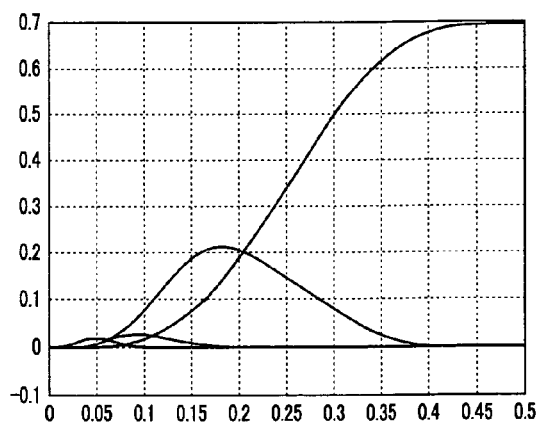
Figure 5F:
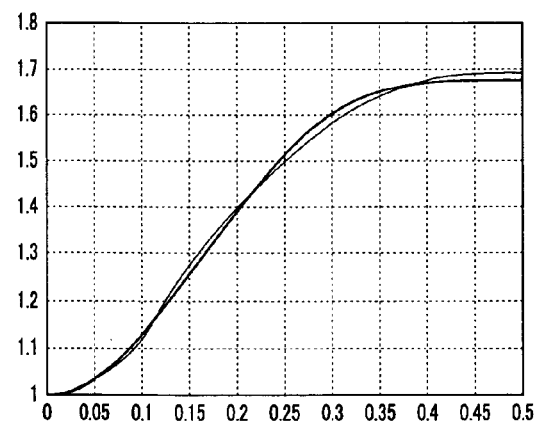

FIGS. 5C to 5E illustrate a method for restoring the MTF. FIG. 5C shows an example of enhancement characteristics for restoring deterioration. In order to produce a filter with these enhancement characteristics, filters with enhancement characteristics shown in FIG. 5D are summed. In other words, a filter with the enhancement characteristics shown in FIG. 5C can be produced by summing the filters shown in FIG. 5D. FIG. 5E shows an example of a filter with these balanced levels. A filter with the characteristics shown in FIG. 5F is produced by adjusting the intensities of the filters such that the filter produced in FIG. 5E has characteristics closer to those shown in FIG. 5C. In this manner, a filter with desirable frequency enhancement characteristics can be produced. These techniques are commonly used for multi-frequency processing, such as a sharpening filter based on the wavelet filter, Laplacian filter, and moving average. A filter with particular enhancement characteristics such as those shown in FIG. 5C can be produced by combining filters with various enhancement characteristics, such as the Laplacian filter, wavelet transform, and sharpening filter. A deteriorated MTF can be restored by applying the filter produced in this manner to image data in the restoring circuit 1016. In this case, a future deterioration in MTF can be estimated in the determining circuit 1015 based on an image-quality evaluating value approximated with a least squares method or a spline curve, and thereby it is possible to determine, for example, when to start restoration.

The following description with reference to FIG. 4 focuses mainly on the portions of the flowchart of FIG. 4 that are different from the flowchart of FIG. 2. Referring to FIG. 4, in steps S407 and S408, the ratio (An/A1) of MTFs at different points in time is calculated, and according to this ratio, a determination is made whether or not the image quality, expressed in terms of MTF, deteriorates. This ratio is used as a sharpness-evaluating value for an image-quality evaluating value. The MTF deteriorates due to, for example, a change in scattered radiation dose resulting from the patient table being replaced or a gap between the fluorescent substance and an imaging element resulting from a portion of the fluorescent substance being peeled off.

If a determination is made that the ratio of MTFs indicates a significant problem (i.e., the result of the image quality test is not acceptable), a further detailed determination in step S411 is made by using the ratio of MTFs at different points in time. If the number of measurement points is greater than a threshold value (n), then in step S412 a least squares approximation is used. If the number of measurement points is less than a threshold value (n), then in step S413 a spline approximation is used. Based on the above-described determination, the determining circuit 1015 determines the current degree of deterioration in image quality, and estimates how much the image quality will deteriorate in the future. Based on this determination and estimation, the extent and the time of restoration by the restoring circuit 1016 are determined. It is noted that in FIG. 5B the same curve is obtained regardless of whether the MTF itself or the ratio of MTFs is used, although the unit of the vertical axis differs between when the MTF itself is used and when the ratio of MTFs is used. For the determination in step S408, another method such as a spline approximation may also be used. A spline approximation advantageously provides a higher determination accuracy than an image-quality evaluating value based on a single point in time.

The restoring circuit 1016 then generates the above-described filter and applies processing for increasing the MTF to the image data in step S414. For this processing, the MTF at a particular point in time is calculated from the ratio of MTFs to determine how much the MTF should be improved.

Figure 6:
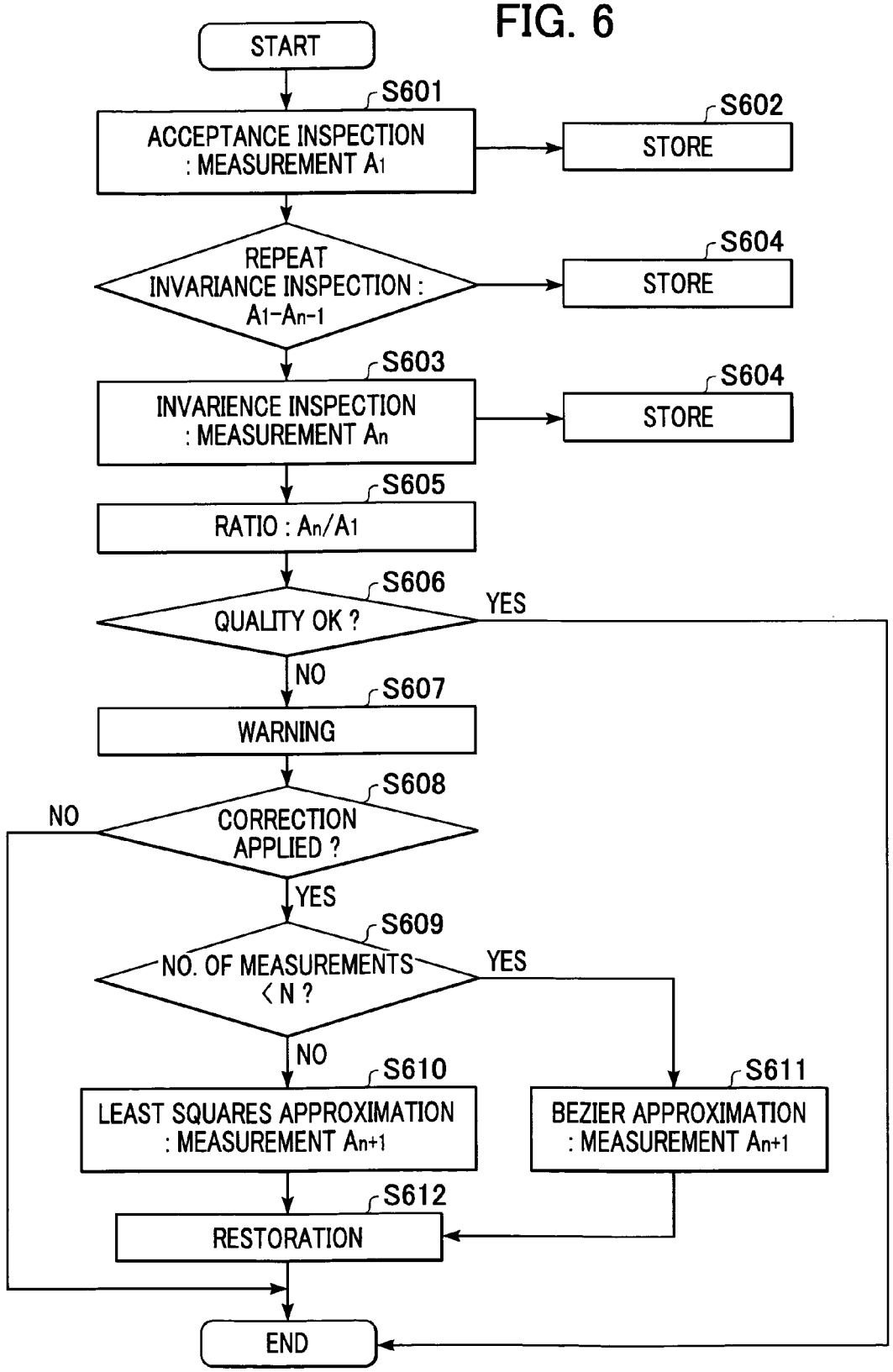
FIG. 6 is a flowchart where a relative sensitivity factor is used as an image-quality evaluating value.
Figure 7A:
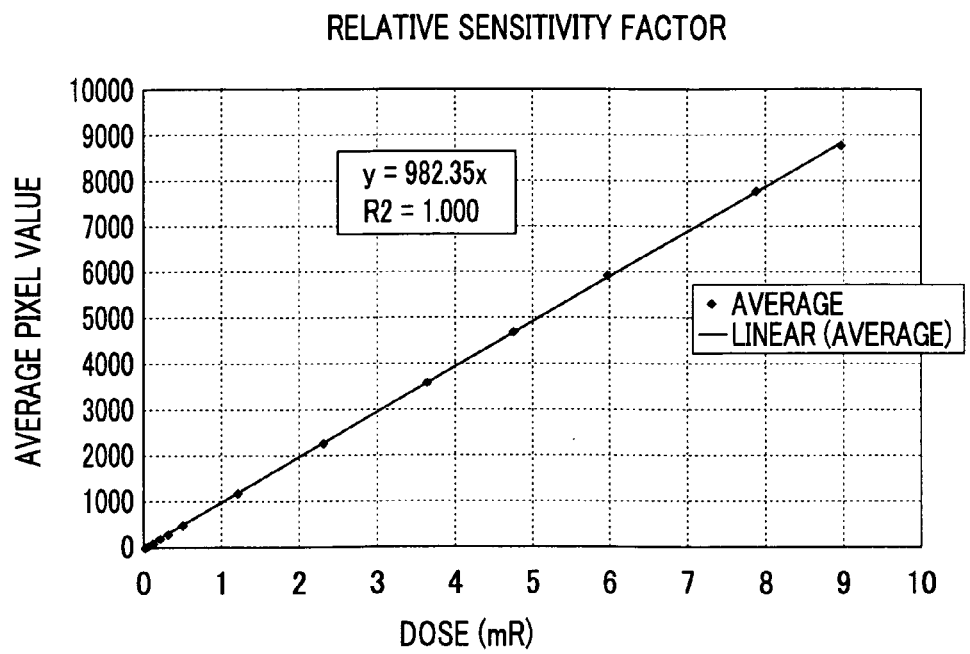
FIGS. 7A and 7B illustrate a relative sensitivity factor.
Figure 7B:
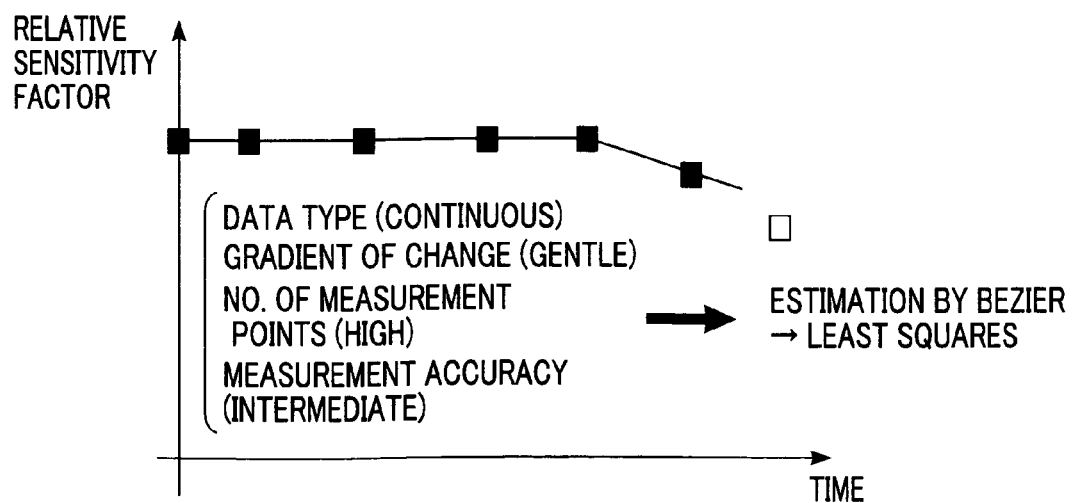

FIG. 6 shows a flowchart diagram for estimating a change in relative sensitivity factor over time with a Bezier approximation for restoration according to this embodiment. The following description focuses mainly on portions of FIG. 6 that are different from the flowcharts of FIGS. 2 and 4. FIG. 7A illustrates the relative sensitivity factor of an imaging element. The horizontal axis represents the dose on the imaging element, and the vertical axis represents the output value from the imaging element in response to the dose. This output value, called a pixel value, forms image data. In the example of FIG. 7A, measurement is performed two or more times to calculate an average pixel value, and thus the vertical axis indicates the average pixel value for each dose. The relative sensitivity factor in this embodiment represents the relationship between a radiation dose and the imaging element, i.e., the gradient of the line in FIG. 7A. FIG. 7B shows an example of a change in relative sensitivity factor over time. The number of defective elements, the sharpness-evaluating value (MTF), or the value of the relative sensitivity factor is used as an image-quality evaluating value in this embodiment. These methods for evaluating the image quality are common, and therefore a detailed description of such methods is omitted.

Referring to FIG. 6, the ratio of relative sensitivity factors is calculated in step S605. Then, in step S606, a determination is made from the ratio as to whether or not there is significant random deterioration in the relative sensitivity factor. In step S606, not only are pixel values compared, but also the measurement environments of the radiography apparatus 1000 are checked for change. In addition to the comparison of pixel values, which are output values from imaging elements, the measurement environments should be taken into consideration to measure the relative sensitivity factor correctly. In particular, an output value of the radiography apparatus 1000 may change depending on the measurement environment, including the temperature, the humidity, the subject distance, the filter type, the size of the radiation field, and the measurement geometry. Thus, it is desirable that the measurement environments be identical across measurements. In short, the following two items are determined in step S606. First, a determination is made as to whether or not the measurement of relative sensitivity factor changes over time. Second, a determination is made as to whether or not the measurement environments are suitable for the measurement of a change in relative sensitivity factor over time. A determination is made as to whether or not some measurement environments (e.g., temperature, humidity, subject distance, filter type, size of the radiation field, measurement geometry) at the time of an invariance test differ from those stored in the previous step. If the measurement environment differs, a message indicating that a relative sensitivity factor cannot be determined may be displayed.

If a determination is made that the relative sensitivity factor indicates a significant problem (i.e., the result of the image quality test is not acceptable), a further detailed determination is made in step S609 by using the ratio of relative sensitivity factors at different points in time. If the number of measurement points is greater than a threshold value (n), then in step S610 a least squares approximation is used. If the number of measurement points is less than a threshold value (n), then in step S611 a Bezier approximation is used. Based on the above-described determination, the determining circuit 1015 determines the current degree of deterioration in image quality, and estimates how much the image quality will deteriorate in the future. Based on this determination and estimation, the extent and the time of restoration by the restoring circuit 1016 are determined. For the determination in step S606, a least squares approximation or a spline approximation may be used.

The procedure for measuring the relative sensitivity factor is carried out in the following order: the conditions for the system of measurement are set identical to those at the time of the acceptance inspection; an image is acquired while the dose at each dose-monitoring point within the dynamic range of the radiography apparatus 1000 is monitored with a dosimeter; the average pixel value in the predetermined area is calculated from the pixel values of the acquired image (step S612 of FIG. 6).

Second Embodiment

A second embodiment will now be described with reference to FIG. 8. In the first embodiment, image-quality evaluating values are determined individually. In contrast, in the second embodiment, associated image-quality evaluating values are integrated into a comprehensive new image-quality evaluating value.

Figure 8:
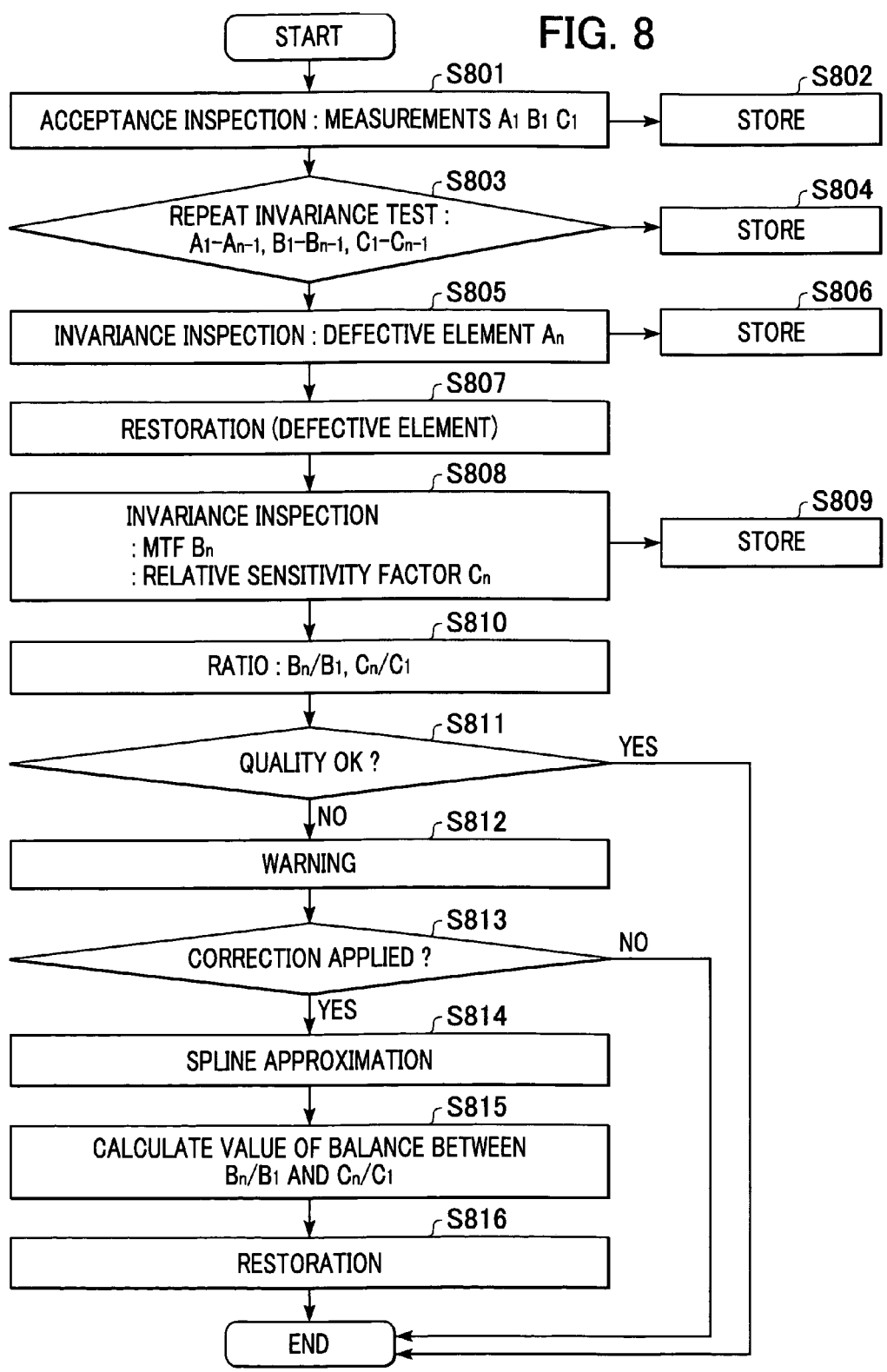
FIG. 8 is a flowchart where the number of defective elements, an MTF, and a relative sensitivity factor are used as image-quality evaluating values.

FIG. 8 is a flowchart illustrating a restoration procedure which is initiated when a change over time in relative sensitivity factor, MTF, or number of defective elements is detected, where the three indices according to the method of the present invention are taken into consideration together.

In steps S801 to S804, measurement is performed in the same manner as described above, except that a plurality of physical quantities are measured together.

Next, in step S805, a check for defective elements is performed. Then, the ratio of MTFs and the ratio of relative sensitivity factors are calculated based on image data acquired after the restoration of the defective elements (step S807) as image-quality evaluating values (steps S808 and S810). The reason that the defective elements are corrected first is because the other image-quality evaluating values, that is, the sharpness-evaluating value and the relative sensitivity factor, are greatly affected by defective elements. The number of defective elements obtained in step S805 is stored in step S806, and the MTF and relative sensitivity factor obtained in step S808 are stored in step S809.

Next, in step S811, a determination is made whether or not the image quality is subjected to a significant variation based on the plurality of image-quality evaluating values. In this case, a determination may be made for each image-quality evaluating value or by using a new image-quality evaluating value that is calculated from the ratio of MTFs and the ratio of relative sensitivity factors. It is noted that a value obtained by weighting sharpness-evaluating values (MTF) at a plurality of frequencies may be used as an image-quality evaluating value, in the same manner as described above. Furthermore, a new image-quality evaluating value may be calculated from many image-quality evaluating values.

In step S814, the determining circuit 1015 determines the current degree of deterioration in image quality, and estimates how much the image quality will deteriorate in the future with a spline approximation of the new image-quality evaluating value obtained from the ratio of MTFs and the ratio of relative sensitivity factors. Then, in steps S815 and S816, the restoring circuit 1016 calculates how much the MTF should be improved for restoration from the result of the above-described determination.

A determination made based on a plurality of image-quality evaluating values, that is, based on more diverse factors, advantageously achieves a more reliable result than a determination based on a single evaluating value.

Third Embodiment

A third embodiment according to the present invention will now be described.

Figure 9:
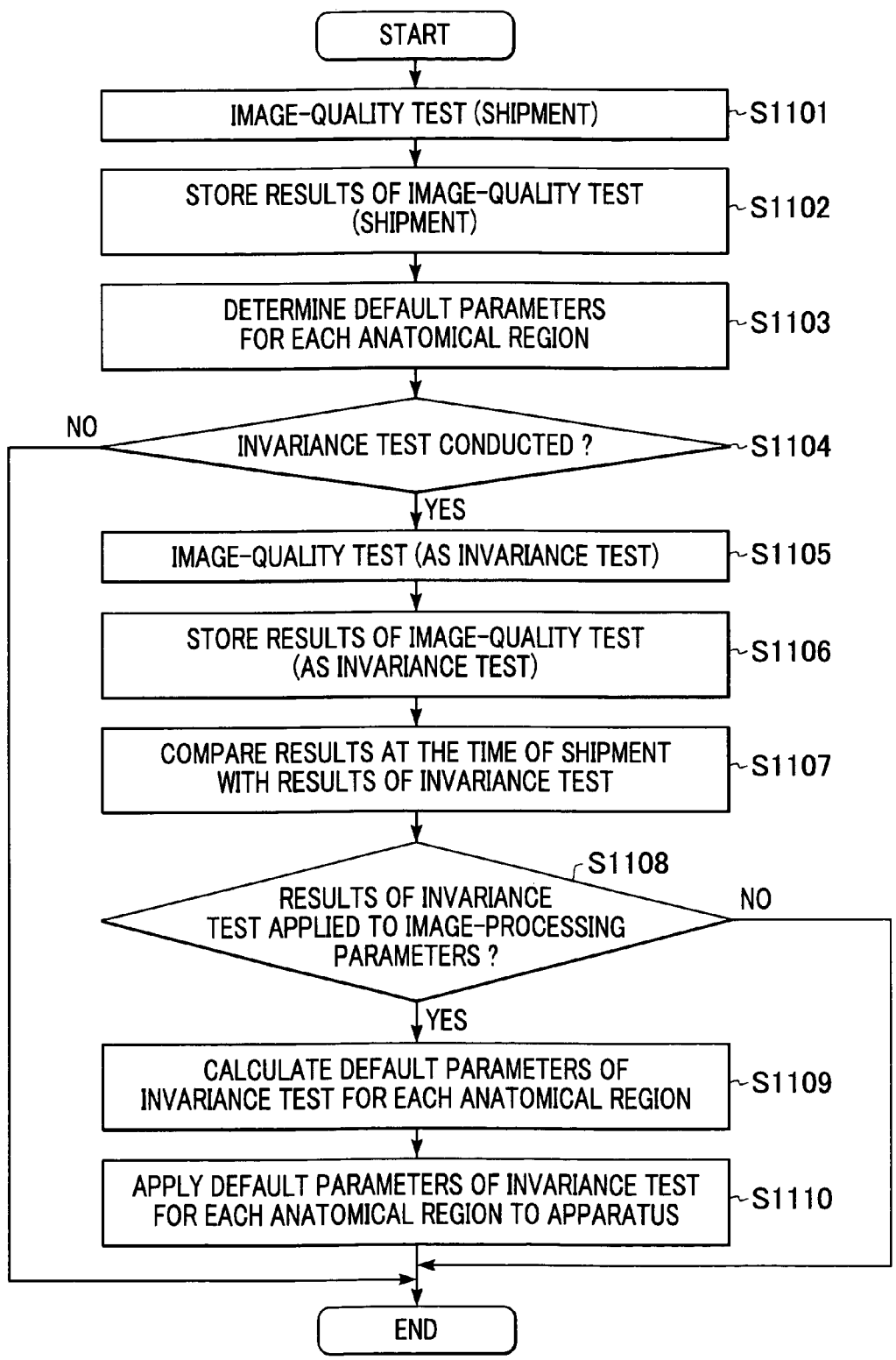
FIG. 9 is a flowchart showing the flow of processing according to a third embodiment.

FIG. 9 is a flowchart for a radiography method by a radiography system according to an embodiment of the present invention.

In an invariance test, the results are compared with the results of the acceptance test carried out at the time of shipment. Thus, the invariance test should be conducted with the same method as in the acceptance test. Turning to FIG. 9, in step S1101, a quality evaluation test is conducted at the time of shipment. Test items for image-quality evaluation include the sharpness, the sensitivity, etc.

The results of the image evaluation test at step S1101 are stored in step S1102 in a storage unit 28, which will be described below. The results of the image-quality evaluation test at the time of shipment are used as criteria for subsequent image-quality evaluation tests carried out for a change in image quality over time, as described below.

In step S1103, the defaults for image-processing parameters for each anatomical region are determined. In general, the defaults of these image-processing parameters differ greatly from facility to facility, such as different hospitals. The defaults of these image-processing parameters for each anatomical region are selected according to the preferences of, for example, users in a hospital. For this purpose, images acquired from a human phantom are output to determine each image-processing parameter at the time of shipment.

It should be noted that the functionality of step S1103 is independent of the functionality and results of steps 1101 and 1102. Thus, the order of step S1103 and the combination of steps S1101 and S1102 can be interchanged.

In step S1104, a determination is made as to whether or not an invariance test is to be conducted.

When a determination is made that an invariance test is conducted at step S1104, a test, such as one for image-quality evaluation, is conducted in step S1105. In this test, the test conditions, the test items, and the test method are identical to those of the acceptance test conducted at the time of shipment in step S1101.

The image-quality evaluating value obtained at the time of the invariance test in step S1105 are stored in the storage unit 28 in step S1106.

In step S1107, the image-quality evaluating value obtained at the time of the invariance test and stored in step S1106 is compared with the image-quality evaluating value stored in step S1102 at the time of the acceptance test.

In step S1108, a determination is made as to whether or not the result of the invariance test is reflected on an image-processing parameter.

If a determination is made in step S1108 that the result of the invariance test is reflected on an image-processing parameter, the default parameters for image-quality processing for each anatomical region at the time of the invariance test are calculated in step S1109. For example, if the test result indicates a change in sensitivity, the gradient of the contrast in the gradation curve is shifted in proportion to the change in the sensitivity. If the test result indicates a change in sharpness (MTF), the enhancement coefficient C for sharpening is changed so as to produce the MTF identical to that at the time of shipment. This method will be described in detail below.

Based on the results of the invariance test calculated in step S1109, the default parameters for image-quality processing for each anatomical region are applied to the radiography apparatus in step S1110.

Figure 10:
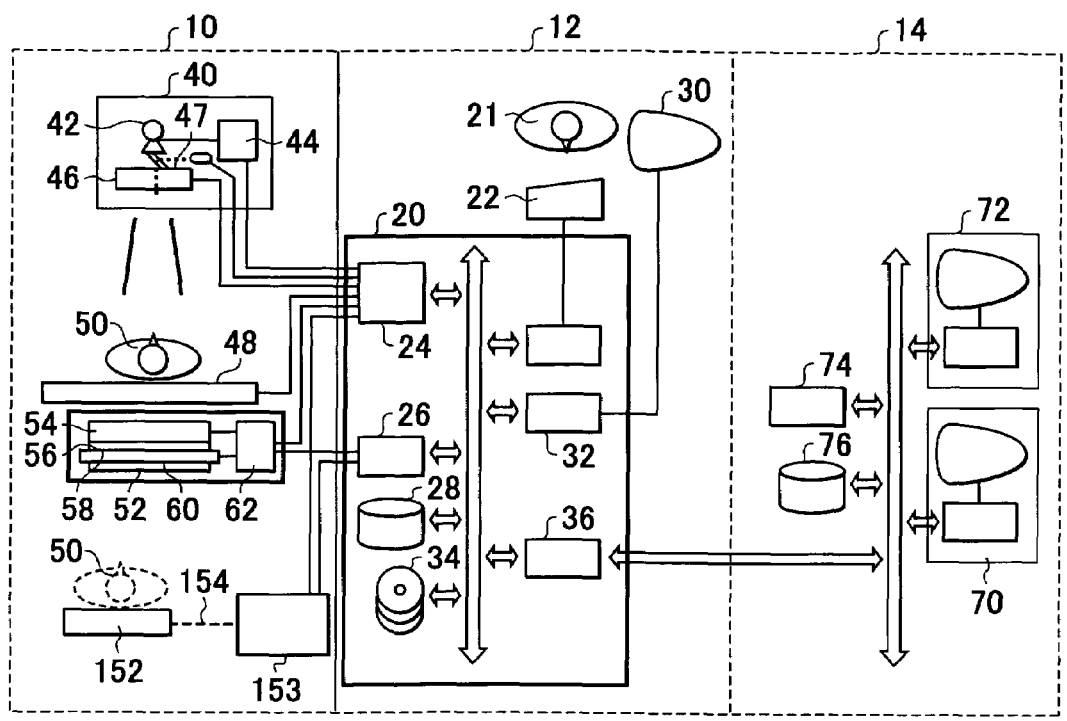
FIG. 10 is a schematic diagram of a radiography system.

FIG. 10 is a block diagram showing the structure of a radiography system realized with an embodiment according to the present invention.

The radiography system includes a radiographic room 10, a radiation control room 12, and clinical room/other operation rooms 14.

The radiation control room 12 in FIG. 10 will now be described. The system controller 20 that controls the entire operation of this radiography system is installed in the radiation control room 12. The operator interface 22, which includes a radiation exposure start switch, a touch panel, a mouse, a keyboard, a joystick, and a footswitch, is used by the operator 21 to enter various instructions into the system controller 20. Instructions given by the operator 21 include the specification of radiographic conditions (e.g., static/dynamic images, the X-ray tube voltage, the tube current, and the irradiation time, etc.), exposure timing, image-processing conditions, an examinee ID, and the method for processing captured images.

The system controller 20 in the radiation control room 12 of FIG. 10 will now be described. The radiographic controller 24 controls the radiography system installed in the radiographic room 10, and the image processor 26 processes the image obtained with the radiography system the radiographic room 10. Image processing by the image processor 26 includes recognition of the radiation field, image data correction, spatial filtering, recursive processing, gradation processing, scattered radiation correction, and dynamic range (DR) compression. The large-capacity, high-speed storage unit 28 stores the basic image data processed by the image processor 26. Storage unit 28 is realized, for example, by a hard disk array such as a RAID. The radiation control room 12 further contains a monitor display 30 (hereinafter, referred to as a monitor) that displays video, a display controller 32 that displays various text and images by controlling the monitor 30, a large-capacity external storage unit 34 (e.g., a magneto-optical disk), and a LAN board 36 that connects units in the radiation control room 12 to units in the clinical room/other operation rooms 14 in order to transfer acquired images in the radiographic room 10 to units in the clinical room/other operation rooms 14.

The radiographic room 10 in FIG. 10 will now be described. A radiation generator 40 that emits a radiation beam is installed in the radiographic room 10. The radiation generator 40 includes an X-ray tube 42 that emits a radiation beam, a high-voltage generator 44 controlled by the radiographic controller 24 to drive the X-ray tube 42, and a radiation diaphragm 46 that collimates a radiation beam generated by the X-ray tube 42 to the desired radiographic field. A subject 50, that is, a patient, lies on a radiographic table 48. The radiographic table 48 is driven according to control signals from the radiographic controller 24 and can change the orientation of the subject 50 with respect to the radiation beam from the radiation generator 40. Below the radiographic table 48 is arranged a radiation detector 52 that detects the radiation beam that has passed through the subject 50 and radiographic table 48.

The structure of the radiation detector 52 in FIG. 10 will now be described. The radiation detector 52 includes a laminate of a grid 54, a scintillator 56, a photodetector array 58, a radiation exposure monitor 60, and a driver 62 that drives the photodetector array 58. The grid 54 reduces the effect of scattered radiation generated through the subject 50. The grid 54 includes members with low radiation absorption and high radiation absorption, such as a stripe structure of Al and Pb. To prevent moire fringing from occurring due to the grid ratio between the photodetector array 58 and the grid 54, the radiation detector 52 vibrates the grid 54 according to the control signal of the driver 62 based on the setting from the radiographic controller 24 at the time of irradiation. Whether or not the grid 54 should be vibrated is selected by the radiographer. Thus, radiography may be performed with the grid 54 fixed. When radiography is performed with the grid 54 fixed, it is desirable that settings which minimize moire fringing, such as aliasing and beat noise resulting from the grid ratio between the photodetector array 58 and the grid 54, be used. In addition, a striped pattern of the grid 54 that appears on an image should be suppressed by decreasing the frequency of such a grid pattern by means of image processing.

In the scintillator 56, the base material of the fluorescent substance is energized (i.e., absorbed) by high-energy radiation, and fluorescence in the visible region occurs due to the recombination energy. In short, radiation is converted into visible light. Some fluorescence occurs from the base materials such as $CaWo_4$ and $CdWo_4$, and other from luminescent center materials, such as CsI:Tl and ZnS:Ag, that are added to the base materials. A columnar crystal of CsI is most commonly used in radiography apparatuses. The structure of this columnar crystal is characterized in that light is easy to propagate in the columnar crystal direction in frontal view. The photodetector array 58 converts visible light generated by the scintillator 56 to an electrical signal.

Furthermore, although the scintillator 56 is separated from the photodetector array 58 according to this embodiment, any detector that directly converts radiation to electrons is also acceptable. For example, a radiation detector that includes a light-receiving portion, such as amorphous Se and $PbI_2$, and amorphous silicon TFT can be used.

The radiation exposure monitor 60 monitors the amount of radiation transmission. The radiation exposure monitor 60 may directly detect radiation with, for example, a light-receiving element of crystalline silicon, or it may detect fluorescence with the scintillator 56. In this embodiment, the radiation exposure monitor 60 includes an amorphous-silicon light-receiving element formed on the bottom surface of the substrate of the photodetector array 58 to detect visible light, proportional to the radiation dose, that has passed through the photodetector array 58 and send the information about the amount of light to the radiographic controller 24. The radiographic controller 24 controls the high-voltage generator 44 based on information from the radiation exposure monitor 60, and adjusts the radiation dose accordingly. The driver 62 drives the photodetector array 58 to read a signal from each pixel under the control of the radiographic controller 24.

The thin radiation detector 152 in FIG. 10 will now be described. In FIG. 10, only one of several available types of sensors is illustrated for the thin radiation detector 152. Other types of sensors, such as sensors with spatial resolution or a radiographic field different from those of the thin radiation detector 152, can also be used. The main difference between the thin radiation detector 152 and the radiation detector 52 is that the thin radiation detector 152 is about 20 mm or less in thickness, which is comparable to a film-screen cassette. Furthermore, the thin radiation detector 152 does not have a built-in grid 54, but does have an incorporated simple power supply and a large-capacity (e.g., from ten images to twenty images) memory, and can exchange an image signal and control with the relay 153 without the use of a cable. A laminate of the scintillator 56, the photodetector array 58, the radiation exposure monitor 60, and the driver 62 that drives the photodetector array 58 are incorporated with the radiation detector 52. The thin X-ray detector 152 is operable with or without a cable 154. The use of the cable 154 achieves high-rate image transfer, and therefore accomplishes acquisition, processing, and checking of images within a shorter period of time after radiography. Another thin radiation detector 152

(not shown) is connected to the system controller 20 via the relay 153 for the purpose of radiography of, for example, patient's four limbs.

The clinical room/other operation rooms 14 in FIG. 10 will now be described. In the clinical room/other operation rooms 14, an HIS/RIS (hospital information system/radiology information system) that sends information about, for example, the subject and the radiography method via the LAN board 36 is installed. In addition, image-processing terminals with video display monitors 70, 72 that process and display images (i.e., dynamic/static images) from the LAN board 36 to assist in diagnosis, an image printer 74, and a file server 76 that stores image data are provided.

A control signal for each device from the system controller 20 can be generated based on instructions from the operator interface 22 in the radiation control room 12 or the image-processing terminals 70, 72 in the clinical room/other operation rooms 14.

The basic operation of the system controller 20 shown in FIG. 10 will now be described. The system controller 20 receives instructions from the operator 21 which result in commands on radiographic conditions being sent to the radiographic controller 24, which controls the sequence of the steps performed by the radiography system. Based on the commands, the radiographic controller 24 drives the radiation generator 40, the radiographic table 48, and the radiation detector 52 to enable a radiological image to be acquired. The image data signal output from the radiation detector 52 is supplied to the image processor 26, subjected to image processing as specified by the operator 21, and displayed on the monitor 30 as an image. Then, the signal is saved in the storage unit 28 as basic image data. Furthermore, the system controller 20, based on the instructions of the operator 21, performs another round of image processing, displays the image resulting from the image processing, transfers the image data to an apparatus on the network, stores the image, performs video display, outputs the image to film, etc.

The basic operation of the system shown in FIG. 10 will now be described along with the flow of a signal. The high-voltage generator 44 of the radiation generator 40 applies a voltage for generating radiation to the X-ray tube 42 according to a control signal from the radiographic controller 24, thereby causing the X-ray tube 42 to generate a radiation beam. The generated radiation beam enters the subject 50, that is, a patient, via the radiation diaphragm 46. The radiation diaphragm 46 is controlled by the radiographic controller 24 according to the location that receives the radiation beam. In other words, the radiation diaphragm 46 shapes the radiation beam to prevent unnecessary irradiation in response to a change in the radiographic field.

The radiation beam output by the radiation generator 40 in FIG. 10 enters the radiation detector 52 through the radiolucent radiographic table 48 and the subject 50 lying on the radiographic table 48. The radiographic table 48 is controlled by the radiographic controller 24 so that the radiation beam passes through various regions of the subject 50 or passes along various orientations through the subject 50.

The grid 54 of the radiation detector 52 in FIG. 10 reduces the effects of scattered radiation generated by the subject 50. To prevent moire fringing from occurring due to the grid ratio between the photodetector array 58 and the grid 54, the radiographic controller 24 vibrates the grid 54 at the irradiation time. In the scintillator 56, the base material of the fluorescent substance is energized (i.e., radiation is absorbed) by high-energy radiation, and fluorescence in the visible region occurs due to the recombination energy. The scintillator 56 disposed adjacent to the photodetector array 58 converts fluorescence generated in the scintillator 56 to an electrical signal. In other words, the scintillator 56 converts the radiological image to a visible-light image, and the photodetector array 58 converts the visible-light image to an electrical signal. The radiation exposure monitor 60 detects visible light, proportional to the radiation dose, which has passed through the photodetector array 58, and supplies the information about the detection level to the radiographic controller 24. The radiographic controller 24 controls the high-voltage generator 44 based on the information about the exposure of this radiation to cut off or adjust the radiation. The driver 62 drives the photodetector array 58 under the control of the radiographic controller 24 to read a pixel signal from each detector.

A pixel signal output from the radiation detector 52 and the thin radiation detector 152 in FIG. 10 is output to the image processor 26 in the radiation control room 12. Because there is a high level of noise resulting from the generation of radiation in the radiographic room 10, the signal transmission path from the radiation detector 52 to the image processor 26 needs to be highly noise proof. More specifically, a digital transmission system with a high level of error-correcting function is necessary, or a shielded twisted-pair cable with a differential driver, or an optical fiber should be used.

Although described in detail below, the image processor 26 in FIG. 10 switches the display format of the image signal according to the commands from the system controller 20. Furthermore, the image processor 26 performs correction of image signals, spatial filtering, and recursive processing in real time, as well as gradation processing, scattered radiation correction, and DR compression. The image processed by the image processor 26 is displayed on the screen of the monitor 30. Along with the real-time image processing, image information (i.e., basic images) that has been subjected to image correction only is stored in the storage unit 28. In addition, based on the instructions of the operator 21, the image information stored in the storage unit 28 is reformatted to conform to a predetermined standard, such as Image Save & Carry (IS&C), and then stored in, for example, the external storage unit 34 or a hard disk in the file server 76.

Units in the radiation control room 12 in FIG. 10 are connected to a LAN (or WAN) via the LAN board 36. A plurality of radiography systems can be connected to the LAN. The LAN board 36 outputs image data according to a predetermined protocol such as Digital Imaging and Communications in Medicine (DICOM). By displaying a high-resolution static image and a dynamic image as image data on the screen of the display of the image-processing terminal 70, 72 connected to the LAN (or WAN), a physician can perform real-time telediagnosis almost at the same time as radiography.

Figure 11:
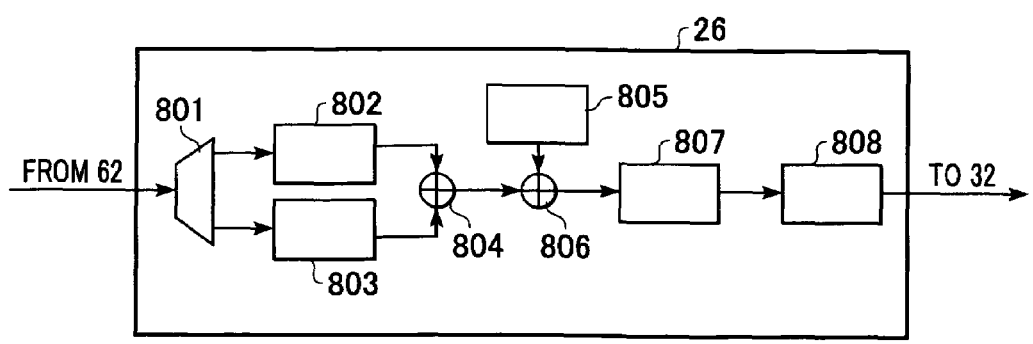
FIG. 11 is a block diagram showing the flow of processing an acquired image.

FIG. 11 shows the image processor 26, along with the flow of image data. The image processor 26 includes a multiplexer 801 that selects a data path, a frame memory 802 for image data, a frame memory 803 for a dark image, an offset correcting circuit 804, a frame memory 805 for gain-correcting data, a gain-correcting circuit 806, a defect-correcting circuit 807, and other image processing circuits 808.

The image data acquired in the image-data acquiring frame (Frxo) in FIG. 11 is stored in the image-data frame memory 802 via the multiplexer 801, and then the correction image acquired in the correction-image acquiring frame (Frno) is stored in the dark-image frame memory 803 via the multiplexer 801 in the same manner. This dark image is used to correct fixed pattern noise in the photodetector array 58. After the dark image has been stored, offset correction, such as Frxo-Frno, is performed by the offset correcting circuit 804, and then the gain-correcting circuit 806 performs gain correction, such as (Frxo-Frno)/Fg, by using pre-acquired gain-correcting data Fg stored in the gain-correcting frame memory 805. The gain correction is performed in order to correct a difference in sensitivity for each pixel of the photodetector array 58. In the description of the present invention, radiography for gain correction may be called calibration or white radiography, whereas gain-correcting data or a gain image may be called a calibration image or a white image. The data thereafter transferred to the defect-correcting circuit 807 is subjected to successive image interpolation to complete sensor-dependant correction processing in accordance with the radiation detector 52, so that an unnatural appearance is prevented from occurring at, for example, dead pixels or at joints in the radiation detector 52 composed of a plurality of panels. Although, in this embodiment, the image processor 26 is included in the system controller 20, the image processing function, which is greatly dependant on the above-described photodetector array 58, may be included in the X-ray detector 52 and the thin radiation detector 152.

Thereafter, in the other image processing circuits 808, standard image processing such as gradation processing, frequency processing, and enhancement are performed, and the processed data is then transferred to the display controller 32 to display it as an acquired image on the monitor 30. The other image processing circuits 808 perform shading correction using the information regarding changes over time, sharpening using the information regarding changes over time, etc.

Figure 12:
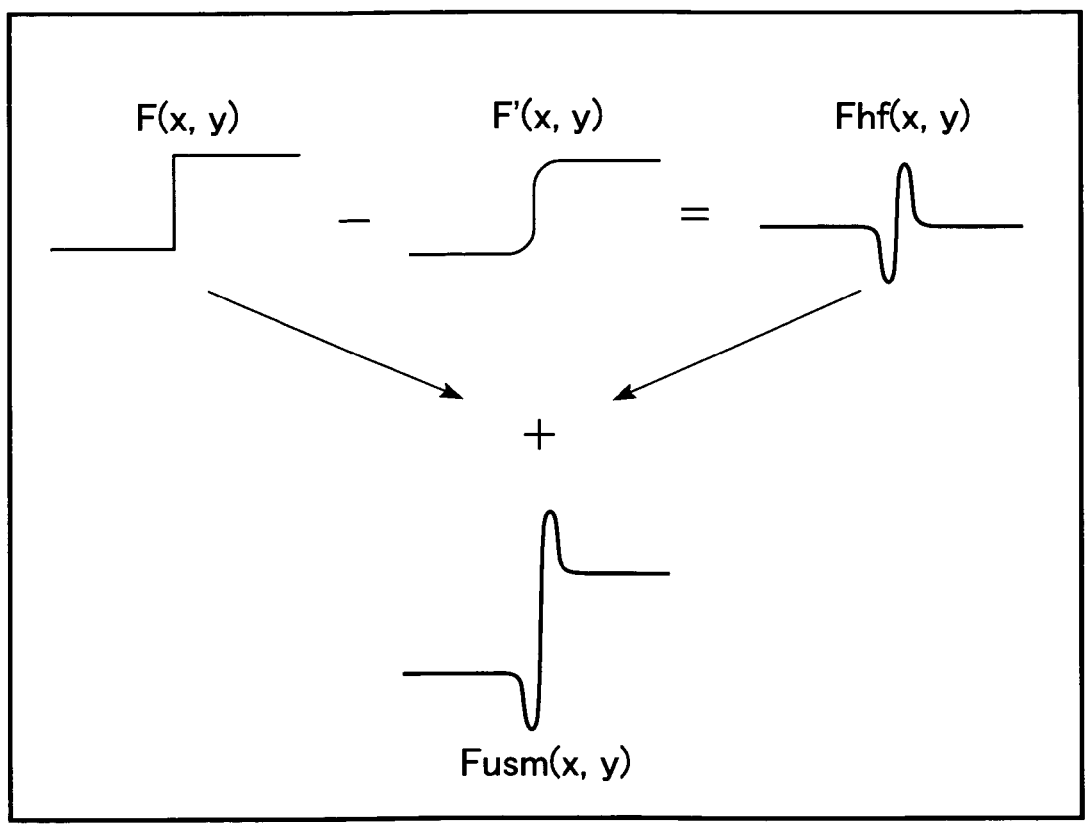
FIG. 12 is a schematic diagram illustrating unsharp masking.

FIG. 12 is a diagram showing the concept of unsharp masking. Unsharp masking used for sharpening will now be described. First, a blurred image F'(x,y) is generated based on an original image F(x,y), and then a high-frequency image Fhf(x,y) is generated by subtracting this blurred image F'(x,y) from the original image F(x,y). An edge-enhanced image Fusm(x,y) is generated by adding this high-frequency image Fhf(x,y) to the original image F(x,y).

Figure 13:
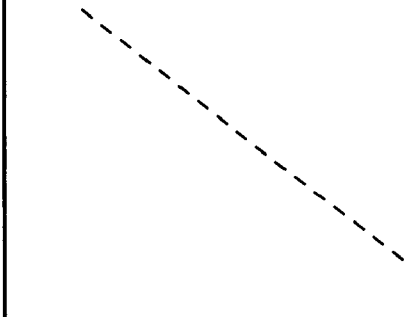
FIG. 13 is a schematic diagram showing a smoothing (spatial) filter.

FIG. 13 is a diagram showing the concept of a smoothing (spatial) filter. To generate the blurred image F'(x,y), the smoothing (spatial) filter of FIG. 13 is used. In short, the smoothing filter is an N×N filter with all coefficients $1/N^2$. Changing the frequency-band parameter causes this N to be changed.

Figure 14:
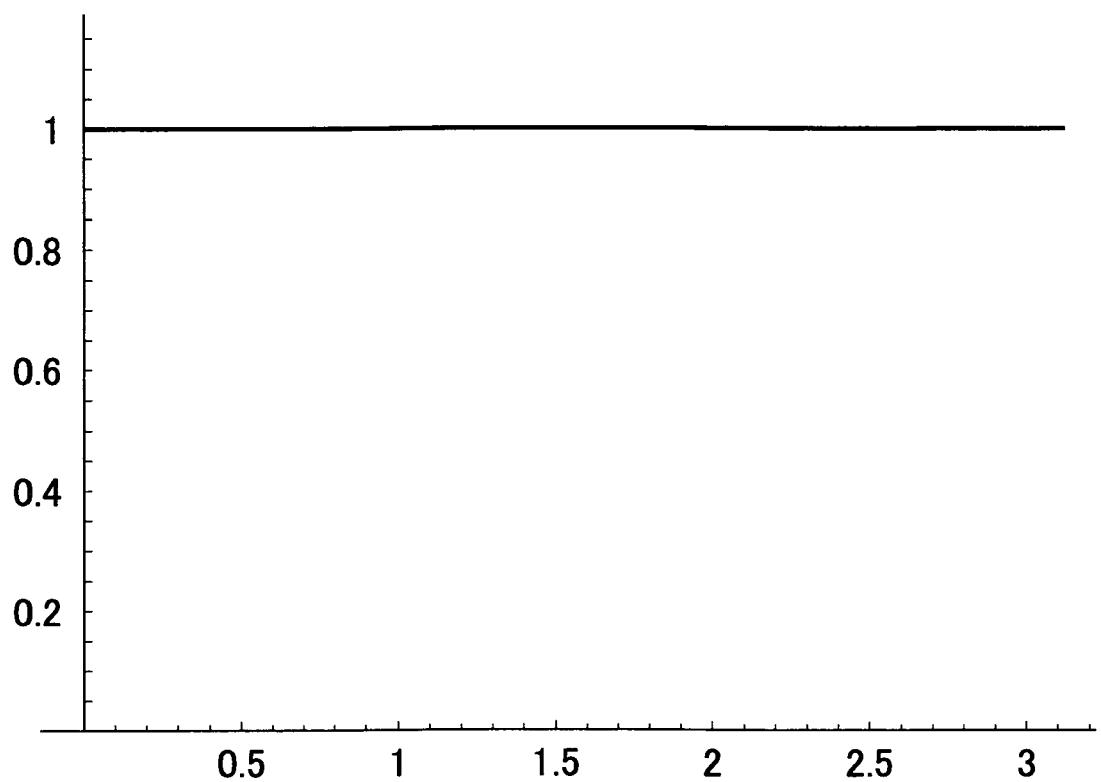
FIG. 14 is a diagram showing the frequency characteristics of an original image.
Figure 15A:
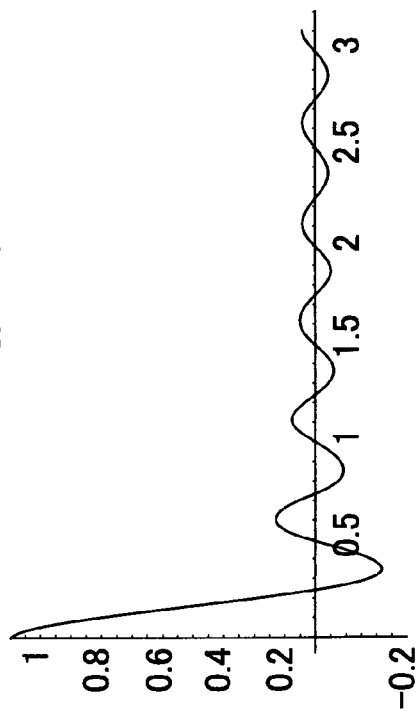
FIGS. 15A to 15D are diagrams showing sinc functions with various frequency characteristics.
Figure 15B:
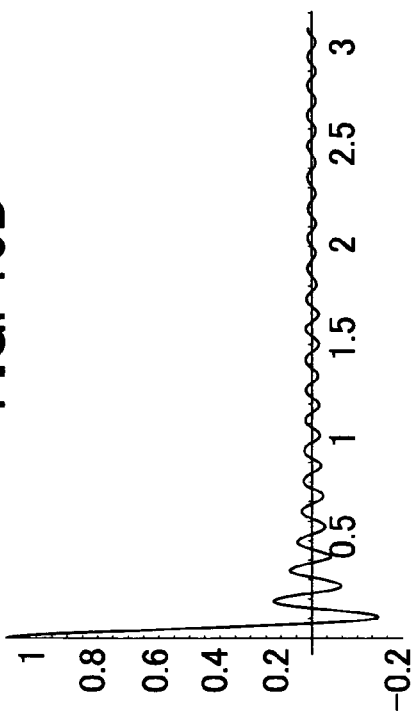
Figure 15C:
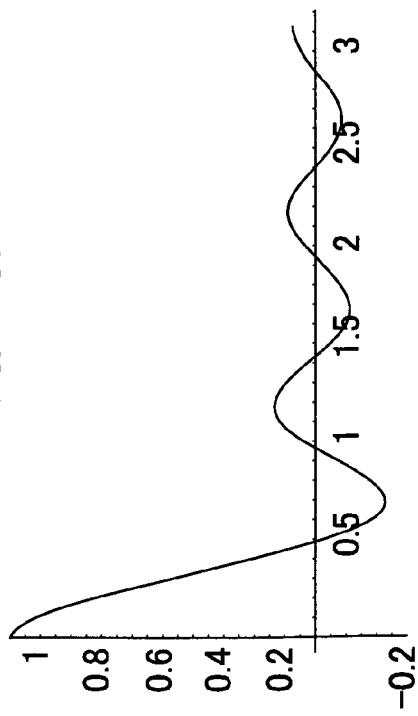
Figure 15D:
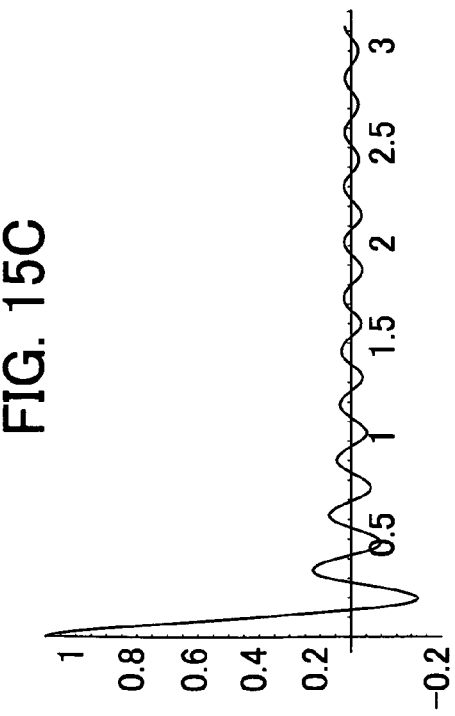
Figure 16:
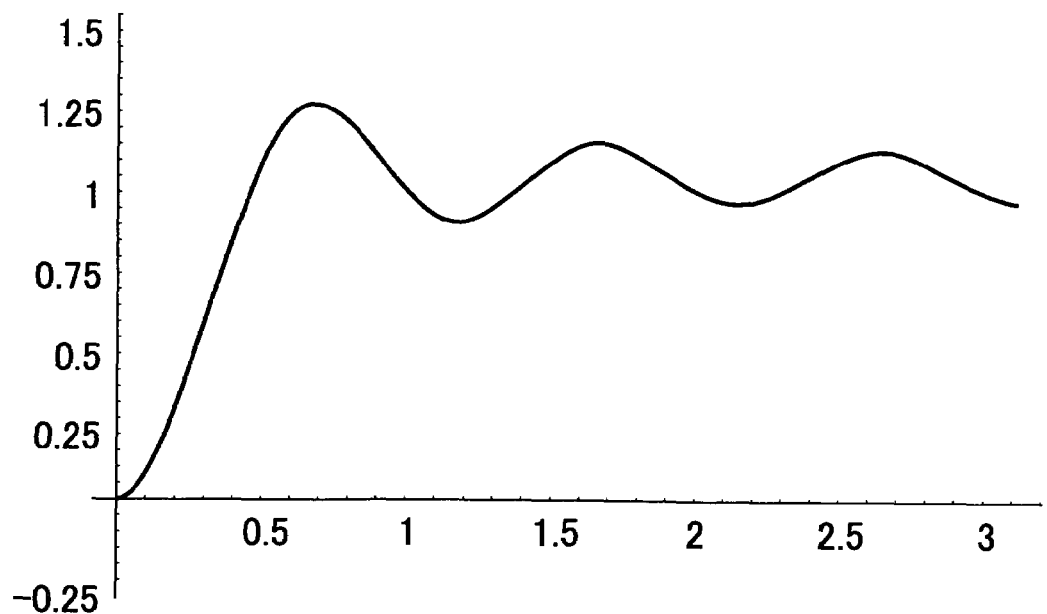
FIG. 16 is a diagram showing the frequency characteristics of a high-frequency image generated by subtracting a blurred image from an original image.
Figure 17:
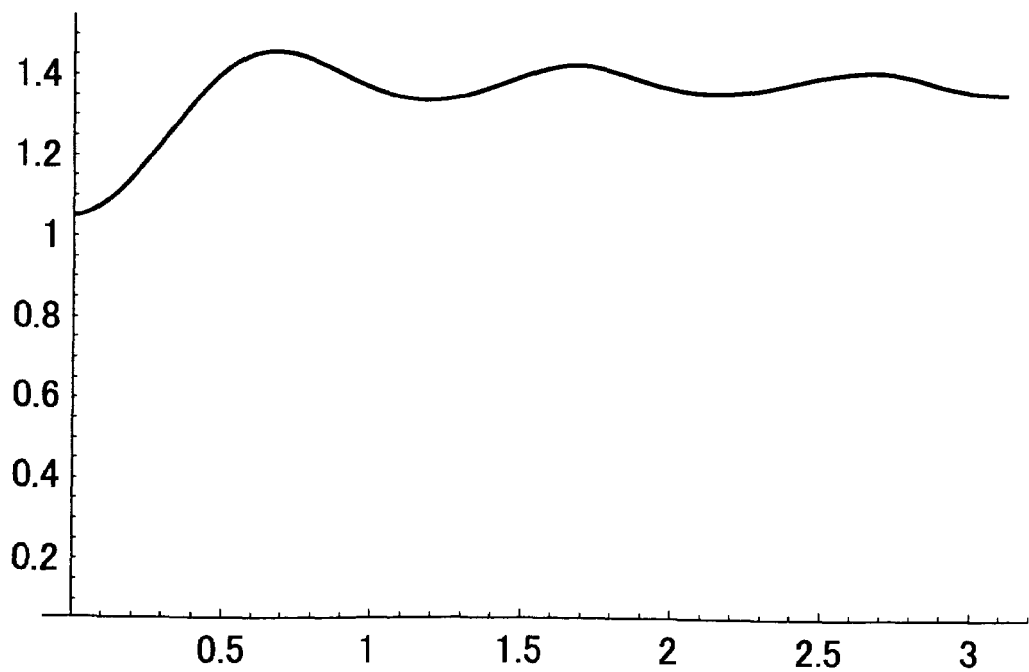
FIG. 17 is a diagram showing the frequency characteristics of an enhanced image generated by adding a high-frequency image to an original image.
Figure 18:
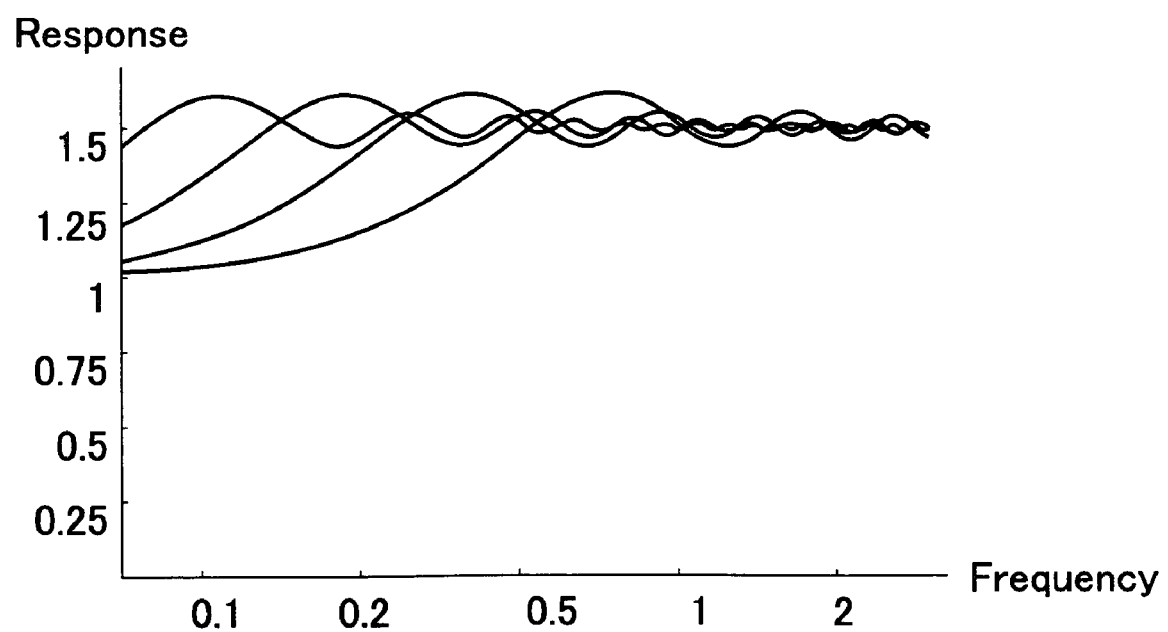
FIG. 18 is a diagram showing the frequency characteristics of an enhanced image generated by adding a high-frequency image to an original image, classified by the degree of enhancement of a sharpening filter.

The above-described frequency-band parameter will now be described with reference to FIGS. 14, 15A to 15D, and 16 to 18. FIG. 14 is a diagram where the frequency characteristics of the original image are 1 at all frequencies. FIGS. 15A to 15D are diagrams showing sinc functions with different frequency characteristics. FIG. 16 shows the frequency characteristics of the high-frequency image generated by subtracting the original image from the blurred image. FIG. 17 shows the frequency characteristics of the enhanced image generated by adding the original image to the high-frequency image. FIG. 18 shows the frequency characteristics of the enhanced image generated by adding the original image to the high-frequency image, analyzed for each parameter. Assuming that the frequency characteristics of the original image are set to 1, as shown in FIG. 14, the frequency characteristics of the blurred image appear as the sinc functions shown in FIGS. 15A to 15D. For unsharp mask N, N=13 in FIG. 15A, N=25 in FIG. 15B, N=45 in FIG. 15C, and N=81 in FIG. 15D. The radiography apparatus allows the frequency-band parameter to be displayed on the monitor 30 as, for example, 9, 7, 5, and 3, so that the technologist who performs image processing can easily adjust the frequency-band parameter. FIG. 16 shows the frequency characteristics of the high-frequency image generated by subtracting this blurred image from the original image. The point with the highest frequency response is the frequency band that is most enhanced. FIG. 17 shows the frequency characteristics of the enhanced image generated by adding the high-frequency image to the original image (in this example, the enhancement coefficient multiplied by 0.33 is added to the original image). FIG. 18 shows a curve for each parameter. Now, the description of unsharp masking is completed.

Figure 19:
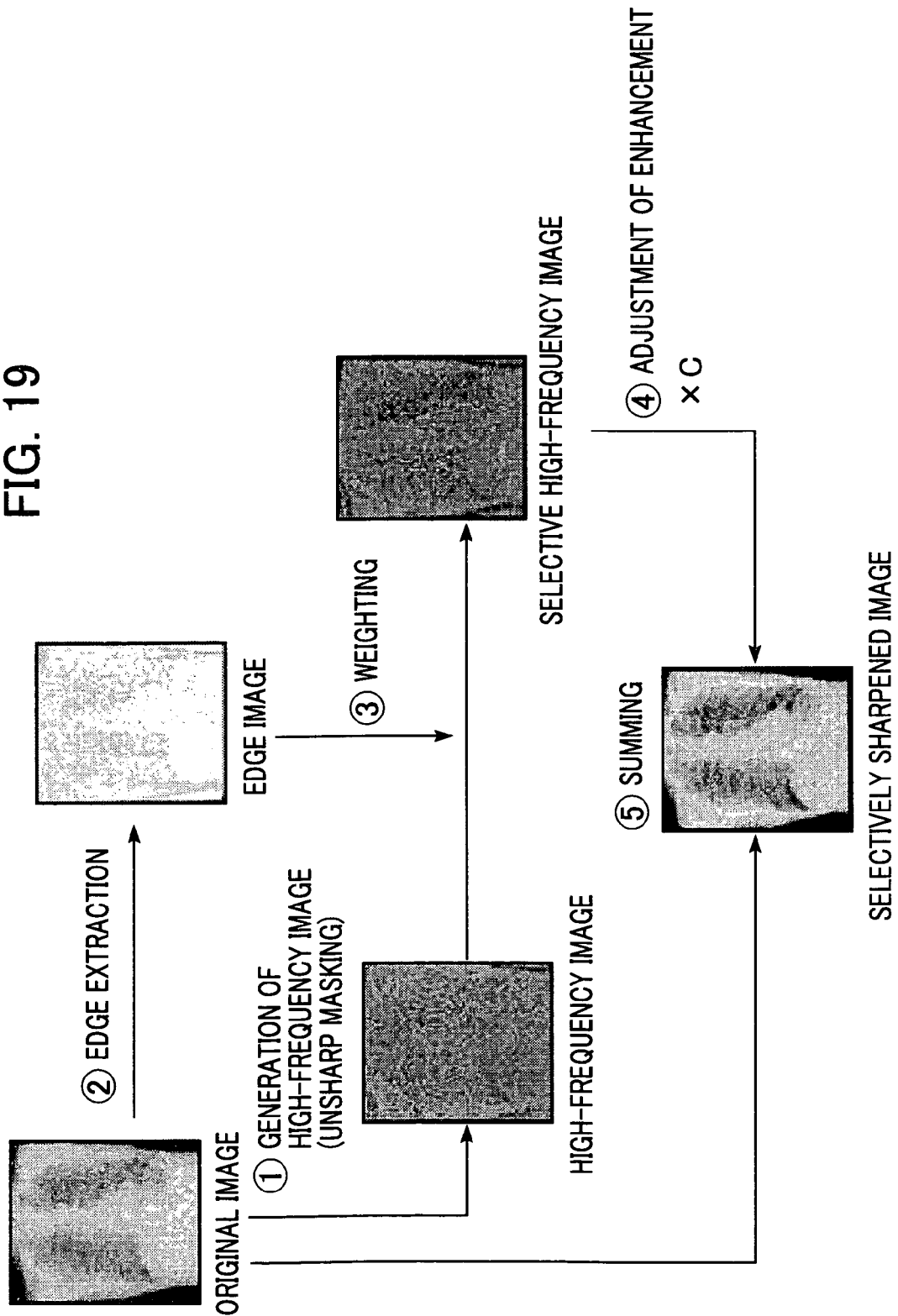
FIG. 19 illustrates sharpening based on unsharp masking.

FIG. 19 illustrates selective sharpening algorithms for preventing enhancement of noise based on unsharp masking. First, a high-frequency-component image is generated based on the original image (step 1). The high-frequency-component image is generated by subtracting the blurred image from the original image, in the same manner as in simple unsharp masking. Then, edges are extracted from the original image (step 2). Based on the extracted edge-enhanced image, weighting is applied to the high-frequency-component image (step 3). With this weighting, structural edges, which should be enhanced, and isolated noise, which should not be enhanced, can be selected. Then, the high-frequency-component image selected with the weighting is multiplied by the enhancement coefficient C (step 4) and is then added to the original image to produce an enhanced image (step 5). This enhancement coefficient C is selected by using an image-quality evaluating value of sharpness in an invariance test. More specifically, the enhancement coefficient C is changed so that the MTF with a frequency distribution close to that of the MTF at the time of the acceptance test can be obtained. In order to obtain the optimal enhancement coefficient C, the value closest to the MTF at the time of the acceptance test is employed in an invariance test, from among MTFs obtained with a least squares approximation. A change in sharpness is caused by, for example, the fluorescent substance coming off. The fluorescent substance and the photodetector are normally attached with, for example, glue. However, due to the effects of, for example, a mechanical impact and temperature/humidity, it is possible that the fluorescent substance comes off or the gap between the fluorescent substance and the photodetector increases. As the above-described gap increases, light diffuses and thereby the sharpness decreases. Thus, if an image-quality evaluating value decreases when an invariance test is carried out, the enhancement coefficient C is set to a higher value. The cause of the MTF being decreased is not limited to the above-described gap. The present invention is also applicable to a change in MTF value due to other factors, including a change in the size of particles in the fluorescent substance or a chemical change in the substance.

Figure 20:
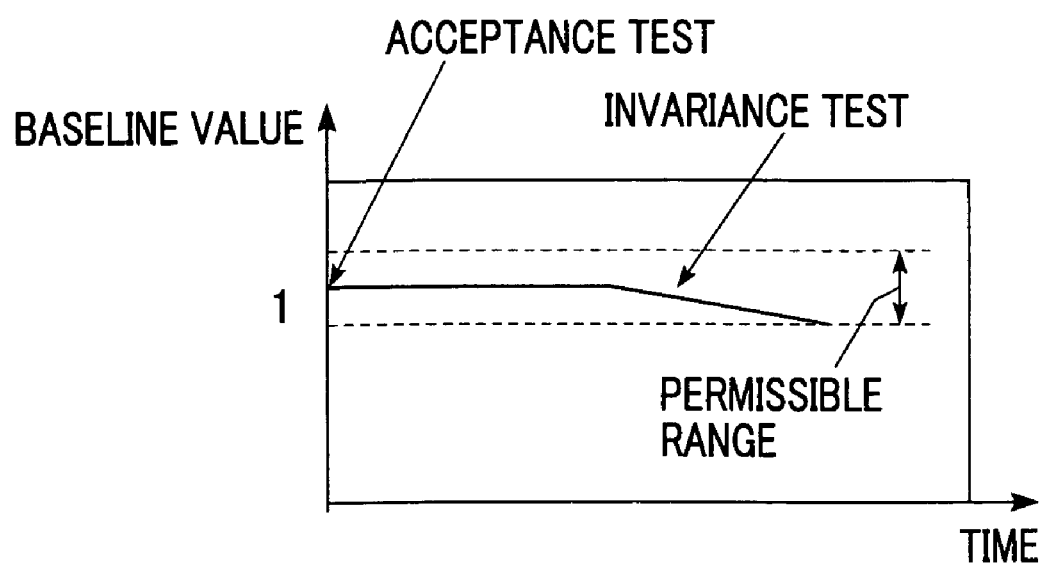
FIG. 20 is a schematic diagram showing a change in image-quality evaluating value over time according to the present invention.

FIG. 20 is a schematic diagram showing a change over time in image-quality evaluating value according to the present invention. In FIG. 20, for example, the sensitivity is presumed to change in terms of an image-quality evaluating value. The sensitivity changes due to, for example, a chemical change in the above-described fluorescent substance resulting from a change in temperature, atmospheric pressure, humidity, etc., in the environment. For example, if the radiography apparatus is exposed to an environment where, for example, temperature, atmospheric pressure, or humidity is outside the operating guidelines for the radiography apparatus, the sensitivity may change accordingly. According to the present invention, the image quality can be brought closer to a value preferable to the user in response to a relative change of the above-described sensitivity by changing image-processing parameters based on the image-quality evaluating values associated with the above-described imaging unit obtained at the time of an invariance test. More specifically, the contrast characteristic curve is changed in response to the above-described sensitivity. If an image-processing parameter that produces the same contrast characteristic curve is still used, regardless of the sensitivity being decreased, images that are output to, for example, film have a wider range of density, resulting in loss of clarity in the peripheral area. This prevents the entire region of interest from being viewed clearly. In other words, if the sensitivity relatively decreases, the same contrast characteristic curve in the above-described image-processing parameter is controlled to be steep. The amount of change in the parameter for the above-described contrast is proportional to the change in the above-described sensitivity. When the above-described contrast characteristic curve is defined as the amount of change in density in response to a change in dose, the parameters are controlled over time so that the product of the above-described contrast and the above-described sensitivity is constant.

Here, a sharpening filter value to be employed based on the sharpness value (i.e., image-quality evaluating value) obtained at the time of an invariance test is not limited to such a sharpening filter value obtained based on the above-described unsharp masking.

In addition, the present invention is applicable to the overall area or part of an image. Furthermore, the purpose of the present invention can also be achieved by supplying a system or an apparatus with a storage/recording medium that records program code of software for achieving the function according to the above-described embodiment and then making a computer (i.e., CPU or MPU) of the system or the apparatus load the program code from the storage medium to execute it. In this case, the program code itself read from the storage medium achieves the function of the above-described embodiment. Thus, a storage medium that records the program code is included in the present invention. As described above, the function of the above-described embodiment is achieved with the execution of the program code read by the computer. In addition, the function of the above-described embodiment may also be achieved by the operating system (OS) running on the computer that performs all or part of the processing according to the commands of the program code. Furthermore, the function of the above-described embodiment may also be achieved such that the program code read from the storage medium is written to a memory provided in an expansion card disposed in the computer or an expansion unit connected to the computer and then the CPU provided on the expansion card or the expansion unit performs all or part of the processing based on commands in the program code.

As many apparently widely different embodiments of the present invention can be made without departing from the spirit and scope thereof, it is to be understood that the invention is not limited to the specific embodiments thereof except as defined in the appended claims.

What is claimed is:

1. A radiography apparatus with a function for evaluating image quality, comprising:
    a radiating-generating unit for emitting radiation;
    an imaging unit for converting the radiation into image data;
    a measuring unit for measuring an image-quality evaluating value of the image data;
    a determining unit for determining the image quality of the imaging unit based on
    a plurality of image-quality evaluating values of the image data acquired at a plurality of points in time, each image-quality evaluating value corresponding to the image data acquired at one of the points in time; and
    a restoring unit for restoring the image data based on the determination,
    wherein the restoring unit restores the image data by using at least one of Laplacian filtering, wavelet transform, and sharpening filtering when at least one of the image-quality evaluating values is a sharpness-evaluating value.

2. The radiography apparatus according to claim 1, wherein the determining unit determines the image quality based on a differential value or a second-order differential value of the plurality of image-quality evaluating values.

3. The radiography apparatus according to claim 1, wherein the determining unit obtains a relationship between the plurality of image-quality evaluating values and corresponding elapsed times and determines the image quality based on the relationship.

4. The radiography apparatus according to claim 1, wherein the determining unit determines the image quality based on a plurality of types of image-quality evaluating values measured at a plurality of points in time.

5. The radiography apparatus according to claim 1, wherein the radiography apparatus utilizes one of a relative sensitivity factor, a sharpness-evaluating value at a particular frequency, and a value obtained by weighting sharpness-evaluating values corresponding to a plurality of frequencies as the image quality evaluating value at each of the points in time.

6. The radiography apparatus according to claim 4, wherein the types of image-quality evaluating values include at least two of a relative sensitivity factor, a sharpness-evaluating value at a particular frequency, and a value obtained by weighting sharpness-evaluating values corresponding to a plurality of frequencies.

7. The radiography apparatus according to claim 1, wherein the imaging unit includes a plurality of imaging elements, and the measuring unit detects a defective element from among the plurality of imaging elements based on the value of the image data and utilizes the number of defective elements as the image-equality evaluating values at each of the points in time.

8. The radiography apparatus according to claim 3, wherein the determining unit obtains the relationship by using one of a spline curve approximation, a least squares method, and a Bezier curve approximation.

9. The radiography apparatus according to claim 1, wherein the restoring unit restores the image data such that the image data exhibits an image-quality evaluating value almost the same as the image-quality evaluating value when the radiography apparatus is used for the first time.

10. The radiography apparatus according to claim 1, wherein the restoring unit restores the image data by using the value of a pixel adjacent to
    a defective element when at least one of the image-quality evaluating values is based on the number of defective elements.

11. The radiography apparatus according to claim 1, wherein the restoring unit estimates a change over time in a plurality of image-quality evaluating values based on a relationship between the plurality of image-quality evaluating values and corresponding elapsed times and performs restoration based on the change.

12. The radiography apparatus according to claim 1, wherein the restoring unit restores the image data by using at least one of Laplacian filtering, wavelet transform, and sharpening filtering when at least one of the image-quality evaluating values is based on a relative sensitivity factor.

13. The radiography apparatus according to claim 1, wherein the imaging unit includes a plurality of imaging elements or a computed radiography device.

14. The radiography apparatus according to claim 1, further comprising a warning display unit for displaying a warning based on the determination.

15. A radiography method with a function for evaluating image quality, comprising the steps of:
emitting radiation;
convening the radiation into image data;
measuring an image-quality evaluating value of the image data;
determining the image quality of the imaging unit based on a plurality of image-quality evaluating values of the image data acquired at a plurality of points in time, each image-quality evaluating value corresponding to the image data acquired at one of the points in time; and
restoring the image data based on the determination,
wherein restores the image data by using at least one of Laplacian filtering, wavelet transform, and sharpening filtering when at least one of the image-quality evaluating values is a sharpness-evaluating value.

* * * * *